US007923017B2

(12) United States Patent
Chaplin et al.

(10) Patent No.: US 7,923,017 B2
(45) Date of Patent: *Apr. 12, 2011

(54) MODIFIED VACCINIA ANKARA VIRUS VARIANT

(75) Inventors: Paul Chaplin, Munich (DE); Paul Howley, Berwick (AU); Christine Meisinger-Henschel, Neuried (DE)

(73) Assignee: Bavarian Nordic A/S, Kvistgaard (DK)

( * ) Notice: Subject to any disclaimer, the term of this patent is extended or adjusted under 35 U.S.C. 154(b) by 514 days.

This patent is subject to a terminal disclaimer.

(21) Appl. No.: 11/977,808

(22) Filed: Oct. 26, 2007

(65) Prior Publication Data

US 2009/0169579 A1 Jul. 2, 2009

Related U.S. Application Data

(60) Division of application No. 11/198,557, filed on Aug. 5, 2005, now Pat. No. 7,384,644, which is a continuation of application No. 10/440,073, filed on May 16, 2003, now Pat. No. 7,189,536, which is a continuation of application No. PCT/EP01/13628, filed on Nov. 22, 2001.

(30) Foreign Application Priority Data

Nov. 23, 2000 (DK) ................................ 2000 01764

(51) Int. Cl.
*A61K 39/285* (2006.01)
*A61K 39/00* (2006.01)
*A61K 39/12* (2006.01)
*A61K 45/00* (2006.01)
*C12N 7/00* (2006.01)
*C12N 7/04* (2006.01)
*A61K 39/21* (2006.01)

(52) U.S. Cl. ................ 424/232.1; 424/184.1; 424/204.1; 424/281.1; 435/235.1; 435/236

(58) Field of Classification Search .................... None
See application file for complete search history.

(56) References Cited

U.S. PATENT DOCUMENTS

| | | | |
|---|---|---|---|
| 5,155,020 A | 10/1992 | Paoletti | 435/69.1 |
| 5,185,146 A | 2/1993 | Altenburger | |
| 5,494,807 A | 2/1996 | Paoletti et al. | 435/69.3 |
| 5,789,245 A | 8/1998 | Dubensky, Jr. et al. | |
| 6,663,871 B1 | 12/2003 | McMichael et al. | |
| 6,761,893 B2 | 7/2004 | Chaplin et al. | 424/199.1 |
| 6,976,752 B2 | 12/2005 | Parish et al. | 347/57 |
| 7,097,842 B2 | 8/2006 | Suter et al. | 424/199.1 |
| 7,189,536 B2 | 3/2007 | Chaplin et al. | |
| 7,445,924 B2 | 11/2008 | Chaplin et al. | |
| 7,459,270 B2 | 12/2008 | Chaplin et al. | |
| 2002/0106798 A1* | 8/2002 | Robinson et al. | 435/456 |
| 2003/0044421 A1* | 3/2003 | Emini et al. | 424/187.1 |
| 2003/0138454 A1 | 7/2003 | Hill et al. | |
| 2004/0131594 A1 | 7/2004 | McMichael et al. | |
| 2005/0214323 A1 | 9/2005 | Chaplin et al. | 424/232.1 |
| 2006/0029619 A1 | 2/2006 | Howley et al. | 424/232.1 |
| 2006/0127984 A1 | 6/2006 | Ackermann et al. | 435/69.1 |
| 2006/0159699 A1 | 7/2006 | Howley et al. | 424/199.1 |
| 2006/0165727 A1 | 7/2006 | Howley et al. | 424/232.1 |
| 2006/0280758 A1 | 12/2006 | Chaplin et al. | 424/232.1 |
| 2010/0119545 A1 | 5/2010 | Chaplin et al. | |

FOREIGN PATENT DOCUMENTS

| | | |
|---|---|---|
| EP | 0836648 B1 | 4/1998 |
| EP | 321679 B1 | 5/2003 |
| EP | 1312678 B1 | 5/2003 |
| WO | WO95/22978 A1 | 8/1995 |
| WO | 96/03144 A1 | 2/1996 |
| WO | WO 97/02355 | 1/1997 |
| WO | WO9702355 A | 2/1997 |
| WO | WO 97/31119 | 8/1997 |
| WO | WO98/13500 A2 | 4/1998 |
| WO | WO 98/56919 | 12/1998 |
| WO | WO 99/07869 | 2/1999 |
| WO | WO 00 39016 | 5/2000 |
| WO | WO 01 68820 | 9/2001 |
| WO | WO 02/24224 | 3/2002 |

OTHER PUBLICATIONS

In the matter of: Certain Modified Vaccinia Ankara ("MVA") Viruses and Vaccines and Pharmacuetical Compositions Based Thereon, Investigation No. 337-TA-550, Commission Opinion on behalf of the Office of the Secretary, Document ID: 270867, United States International Trade Commission, Washington, D.C., Mar. 6, 2007.*
Bowie et al., Deciphering the Message in Protein Sequences: Tolerance to Amino Acid Substitutions, 1990, Science, vol. 247, No. 4948, pp. 1306-1310.*

(Continued)

*Primary Examiner* — Zachariah Lucas
*Assistant Examiner* — Benjamin P Blumel
(74) *Attorney, Agent, or Firm* — Law Office of Salvatore Arrigo and Scott Lee, LLP

(57) ABSTRACT

The present invention provides an attenuated virus, which is derived from Modified Vaccinia Ankara virus, wherein the MVA-BN virus, or a derivative thereof, induces at least substantially the same level of immunity in vaccinia virus prime/vaccina virus boost regimes when compared to DNA prime/vaccinia virus boost regimes. It further describes recombinant viruses derived from this virus and the use of the virus, or its recombinants, as a medicament or vaccine. A method is provided for inducing an immune response in individuals who may be immune-compromised, receiving antiviral therapy, or have a pre-existing immunity to the vaccine virus.

16 Claims, 5 Drawing Sheets

OTHER PUBLICATIONS

Figure 1A:
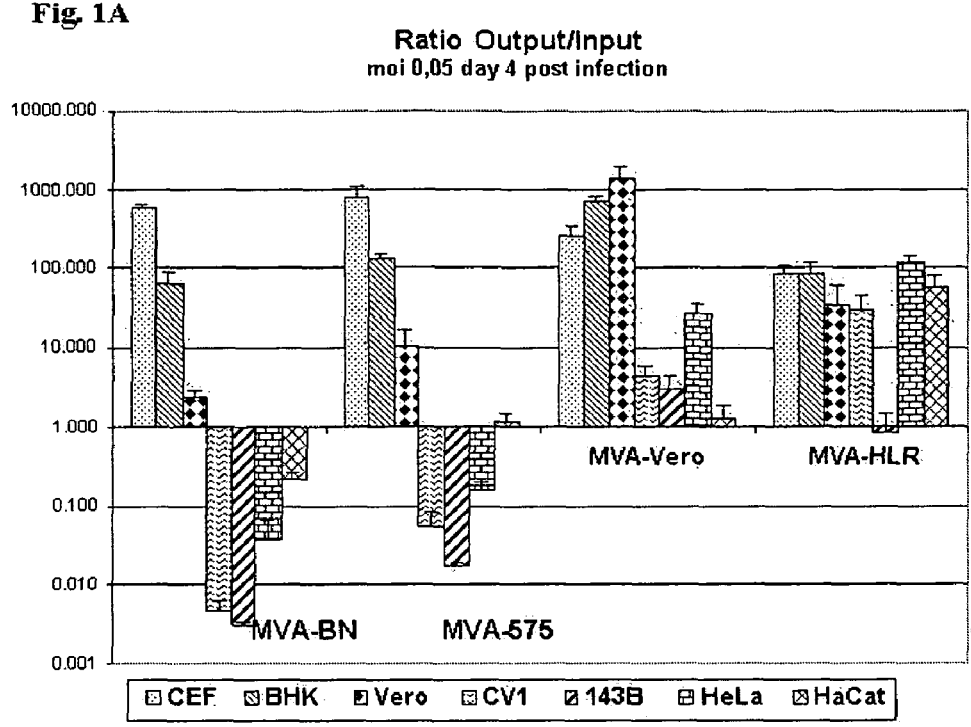

Johnston et al., Current Concepts: An HIV Vaccine-Evolving Concepts, 2007, New England Journal Of Medicine, vol. 356, No. 20, pp. 2073-2081.

In the matter of: Certain Modified Vaccinia Ankara ("MVA") Viruses and Vaccines and Pharmacuetical Compositions Based Thereon, Investigation No. 337-TA-550, Commission Opinion on behalf of the Office of the Secretary, Document ID: 270867, United States International Trade Commission, Washington, D.C., Mar. 6, 2007.

Ambrosini et al., Gene Transfer in Astrocytes: Comparison Between Different Delivering Methods and Expression of the HIV-1 Protein Nef, 1999, Journal of Neuroscience Research, vol. 55, pp. 569-577.

Moss et al. "Host range restricted, non-replicating vaccinia virus vectors as vaccine candidates." Advances in Experimentaly Medicine and Biology 397:7-13, 1996.

Wyatt et al (PNAS 101:4590-4595, 2004).

Earl et al (Nature 428:182-185, 2004).

Eo et al, The Journal of Immunology 166:5473-5479, May 2001.

Holzer et al (Journal of Virology 73:4536-4542, 1999).

Antoine et al (Virology 244:365-96, 1998).

Gilbert et al (Biol. Chem. 380:299-303, 1999).

In the matter of: Certain Modified Vaccinia Ankara ("MVA") Viruses and Vaccines and Pharmaceutical Compositions Based Thereon, Investigation No. 337-TA-550. *Order No. 28: Denying in Part Complainant's Motion for Summary Determination and Denying in Part Respondent's Motion for Summary Determination*, United States International Trade Commission, Washington, D.C., Apr. 18, 2006.

In the matter of: Certain Modified Vaccinia Ankara ("MVA") Viruses and Vaccines and Pharmaceutical Compositions Based Thereon, Investigation No. 337-TA-550, *Nucleotide alignment of MVA-Antione vs Acambis 3000 MVA vs MVA-BN*, Aug. 31, 2005.

In the matter of: Certain Modified Vaccinia Ankara ("MVA") Viruses and Vaccines and Pharmaceutical Compositions Based Thereon, Investigation No. 337-TA-550, *Respondent's Amended Pre-Hearing Brief*, United States International Trade Commission, Washington, D.C., May 8, 2006.

In the matter of: Certain Modified Vaccinia Ankara ("MVA") Viruses and Vaccines and Pharmaceutical Compositions Based Thereon, Investigation No. 337-TA-550, *Respondent's Opposition to Compainant's Motion for Sanctions*, United States International Trade Commission, Washington, D.C., Jul. 7, 2006.

In the matter of: Certain Modified Vaccinia Ankara ("MVA") Viruses and Vaccines and Pharmaceutical Compositions Based Thereon, Investigation No. 337-TA-550, *Respondent's Opposition to Compainant's Motion for Summary Determination of Infringement*, 10439953.051603 United States International Trade Commission, Washington, D.C.

In the matter of: Certain Modified Vaccinia Ankara ("MVA") Viruses and Vaccines and Pharmaceutical Compositions Based Thereon, Investigation No. 337-TA-550, *Respondent's Rebuttal to Compainant's Proposed Conclusions of Law*, United States International Trade Commission, Washington, D.C., Jun. 14, 2006.

In the maater of: Certain Modified Vaccinia Ankara ("MVA") Viruses and Vaccines and Parmaceutical Compositions Based Thereon, Investigation No. 337-TA-550, *Compainant Bavariian Nordic's Motion for Santions and Memorandum in Support of Its Motion*, United States International Trade Commission, Washington, D.C., Jun. 21, 2006 (Public Version).

In the matter of: Certain Modified Vaccinia Ankara ("MVA") Visuses and Vaccines and Parmaceutical Compositions Based Thereon, Investigation No. 337-TA-550, *Memorandum in Opposition to Respondent's Motion for Summary Determination*, United States International Trade Commission, Washington, D.C., Mar. 30, 2006 (Public Version).

In the matter of: Certain Modified Vaccinia Ankara ("MVA") Viruses and Vaccines and Pharmaceutical Compositions Based Thereon, Investigation No. 337-TA-550, *Compainant Bavarian Nordic's Memorandum in Support of Its Motion in Limine*, United States International Trade Commission, Washington, D.C., May 1, 2006 (Public Version).

In the matter of: Certain Modified Vaccinia Ankara ("MVA") Viruses and Vaccines and Pharmaceutical Compositions Based Thereon, Investigation No. 337-TA-550, *Compainant's Post Hearing Brief*, United States International Trade Commission, Washington, D.C., Apr. 28, 2006 (Public Version).

In the matter of: Certain Modified Vaccinia Ankara ("MVA") Viruses and Vaccines and Pharmaceutical Compositions Based Thereon, Investigation No. 337-TA-550, *Compainant Bavarian Nordic's Motion for Summary Determination of Infringement of the '893 Patent, Its Memorandum of Law in Support of Its Motion, Its Statement of Undisputed Facts in Support of Its Motion and Supporting Exhibits*, United States International Trade Commission, Washington, D.C., Mar. 20, 2005 (Public Version).

In the matter of: Certain Modified Vaccinia Ankara ("MVA") Viruses and Vaccines and Pharmaceutical Compositions Based Thereon, Investigation No. 337-TA-550, *Compainant's Post Hearing Reply Brief*, United States International Trade Commission, Washington, D.C., Jun. 14, 2006 (Public Version).

Bender, et al., Oral Immunization with a Replication-Deficient Recombinant Vaccinia Virus Protects Mice Against Influenza. (1996) J. Virology, vol. 70(9):6418-6424.

*Jax® Mice Data Sheet*, Product Information for Stock No. 001913, The Jackson Laboratory, Bar Harbor, Maine, USA.

*List of Documents Relied on in European Opposition Proceedings*, two (2) pages.

Drillien, et al, Attenuation Profile Comparison of Various MVA Strains. Study Report, Institut de Génétique et de Biologie Moléculaire et Cellulaire, Illkirch, France, Feb. 22, 2006.

Hülsemann, et al., Attenuation Profile Comparison of Various MVA Strains. Project #1050, Bavarian Nordic GmbH, Martinsried, Germany, Jan. 2006.

"Analysis of different strains of Modified Vaccinia virus Ankara (MVA) regarding their capability to grow and replicate in various cell lines." *VIVACS Final Report*, Project #1200104, VIVACS GmbH, Martinsried, Germany.

"Determination of various growth characteristics of different Vaccinia virus strains." *VIVACS Study Plan*, Project #0100506 and *VIVACS Study Report*, SR-0100506-01, VIVACS GmbH, Martinsried, Germany, Feb. 2006.

"Determination of various growth characteristics of different MVA strains." *VIVACS Study Plan*, Project #1200405, *VIVACS Study Report*, SR-1200405-00, *Amendment to VIVACS Study Report*, SR-AM-1200405-00, *Amendment to VIVACS Study Report*, SR-AM-1200405-00, VIVACS GmbH, Martinsried, Germany, Jan. 2006.

Zinkernagel, et al., "Attenuation Profile Comparison of Various MVA-strains." *Study Report* UA_02_06, University of Zurich, Zurich Switzerland, Mar. 2006.

Antione, G. "Differences in DNA sequence of MVA Acambis (AY603355) relative to MVA Antione et al (U94848)." *Baxter Report* -Mar. 31, 2006.

Antione, et al., Corrigendum to "The complete genomic sequence of the Modified Vaccinia Ankara (MVA) strain: comparison with other orthopoxviruses" Virology 244 (1998) 365-396 *BAXTER Bioscience*, BO08572.

"PCR-Amplification and Double Strand Sequencing of Five Genomic Regions of M4-MVA (U94848, NCBI Accession number)." *Analytical Report*, Project No. KN-639, GATC Biotech AG, Konstanz, Germany, May 9, 2006.

Sequence Report-MVA 572, Sequiserve, Vetterstetten, Germany, Jul. 6, 2006.

Sequence Report-MVA-1721, Sequiserve, Vetterstetten, Germany, Jul. 6, 2006.

Drexler, et al., J. Gen. Virol. (1998) 79:347-352.

International Preliminary Examination Report, dated Jan. 11, 2006, four pages.

Tartaglia, et al. "NYVAC: a highly attenuated strain of vaccinia virus" Virology 1992, vol. 188, pp. 217-232.

Kovarik, et al. "Induction of adult-like antibody, Th1, and CTL responses to measles hemagglutinin by early life murine immunization with an attenuated vaccinia-derived NYVAC (K1L) viral vector" Virology Jun. 20, 2001, vol. 285, pp. 12-20.

Kazanhi, et al. "Immunogenicity and protective efficacy of recombinant human T-cell leukaemia/lymphoma virus type 1 NYVAC and naked DNA vaccine candidates in squirrel monkeys (*Saimiri sciureus*)" Journal of Virology, Jul. 2001, vol. 75(13), pp. 5939-5948.

Danish Search Report: PA 2000 01764/P2/FRE: Oct. 27, 2001, With Translation.
International Search Report: PCT EP01/13628: May 24, 2002.
International Preliminary Examination Report: PCT/EP01/13628: Mar. 25, 2003.
Mayr, A., Zbl Vet B 23, 417-430 (1976).
Blanchard, J.T., et al., Journal of General Virology, 79, 1159-1167 (1998).
Caroll, W.M. and Moss, B., Virology 238, 198-211 (1997).
Meyer, H., et al., Journal of general virology, 72, 1031-1038 (1991).
Bender, et al., Journal of Virology, vol. 70, No. 9, pp. 6418-6424 (Sep. 1, 1996).
Schneider, et al. (1998), Nature Medicine 4, 397-402.
Sutter, et al. (1994), Vaccine 12, 1032-1040.
Bechera AK. Kumar M, Lockey RF and Mohapatra SS (2002) Hum. Gene Ther. Sep. 20; 13(14):1697-709.
Belyakov IM, Earl P, Dzutsev A, Kuznetsov VA, Lemon M, Wyatt LS, Snyder JT, Ahlers JD, Franchini G, Moss B and Berzofsky JA. (2003) Proc. Natl. Acad. Sci. 100:9458-9463.
Hanke T, Samuel RV, Blanchard TJ, Neumann VC, Allen TM, Boyson JE, Sharpe SA, Cook N, Smith GL, Watkins DI, Cranage MP and McMichael AJ (1999) Journal of Virology 73:7524-7532.
Schneider J, Gilbert SC, Blanchard TJ, Hanke T, Robson KJ, Hannan CM, Becker M, Sinden R, Smith GL and Hill AVS. (1998) Nature Medicine 4: 397-402.
Stittelaar, et al, Vaccine 19:3700-3709, 2001.
Sutter and Moss Proc. Natl. Acad. Sci. USA 89:10847-51, 1992.
Schieflinger, et al, Proc. Natl. Acad. Sci. USA 89:9977-81, 1992.
Merchlinsky, et al. Virology 190:522-6, 1992.
Oxford Biomedica PLC et al, Defendants' Answer to Plaintiff's First Amended Complaint and Counterclaims, Case No. 08cv1156-MMA (RBB), Jun. 1, 2009.
Bavarian Nordic A/S, Plaintiff's Answers to Defendants' Counterclaims, Case No. 08cv1156-MMA (RBB), Jun. 22, 2009.
Bavarian Nordic A/S, Plaintiff's Motion for Partial Summary Judgement on Inequitable Conduct, Case No. 08cv1156-MMA (RBB), Jan. 25, 2010.
Declaration of Theodore J. Folkman, Case No. 08cv1156-MMA (RBB), Jan. 25, 2010.
Suter et al, Modified vaccinia Ankara strains with identical coding sequences actually represent complex mixtures of viruses that determine the biological properties of each strain, Vaccine 27:7442-7450 (2009).
Dr. Elfriede Dworak of the Commercial Court of Vienna, Austria, Decision on Initial Matter, without prejudice, in Case 19Cg 25/06g, May 31, 2007.
Dr. Paul Chaplin, ITC Testimony, ITC Investigation No. 337-TA-550, 447-706, May 10, 2006.
Paul Luckern, ALJ, Order No. 5, ITC Investigation No. 337-TA-550, Jun. 29, 2007.
Oxford Biomedica (UK) Ltd, Opposition to EP Patent No. 1335987, Additional Submissions, Dec. 7, 2009.
Bavarian Nordic, Opposition to EP Patent No. 1335987, Reply to Submissions, Jun. 18, 2008.
Oxford Biomedica (UK) LTD, Opposition to EP Patent No. 1335987, Reply to Patentee's Response, Jan. 28, 2008.
Emergent Product Development Germany GMBH, Opposition to EP Patent No. 1335987, Submission to Patentee's Observations, Mar. 12, 2008.
Bavarian Nordic, Opposition to EP Patent No. 1335987, Response to Oppositions, Aug. 1, 2007.
Emergent Product Development Germany GMBH, Opposition to EP Patent No. 1335987, Notice of Opposition, Sep. 28, 2006.
Virbac SA, Opposition to EP Patent No. 1335987, Notice of Opposition, Sep. 28, 2006.
Innogenetics NV, Opposition to EP Patent No. 1335987, Notice of Opposition, Sep. 27, 2006.
Oxford Biomedica (UK) LTD, Opposition to EP Patent No. 1335987, Notice of Opposition, Sep. 26, 2006.
Baxter AG, Opposition to EP Patent No. 1335987, Notice of Opposition, May 15, 2006.
Sanofi Pasteur Inc, Opposition to EP Patent No. 1335987, Notice of Opposition, Sep. 26, 2006.
Acambis PLC, Opposition to EP Patent No. 1335987, Notice of Opposition, May 15, 2006.
Baxter A/G & Baxter Healthcare SA, Opposition to EP Patent No. 1335987, Response, Aug. 9, 2010.
EPO Opposition Division, Opposition to EP Patent No. 1335987, Preliminary Opinion, Oct. 8, 2009.
Bavarian Nordic A/S, Opposition to EP Patent No. 1335987, Response, Aug. 9, 2010.
Okeke et al., Modified vaccinia virus Ankara multiples in rat IEC-6 cells and limited production of mature virions occurs in other mammalian cell lines, J. Gen Virol. 87:21-27 (2006).
Earl et al., Generation of Recombinant Vaccinia Viruses, Current Protocols in Molecular Biology 16.17.1-16.17.19 (1998).
Chaplin et al, Amended Patent Claims from Oral Proceeding, Opposition to EP Patent No. 1335987, Oct. 5, 2010.
Chaplin et al, Amended Specification from Oral Proceeding, Opposition to EP Patent No. 1335987, Oct. 5, 2010.
Baxter A/G & Baxter Healthcare SA, Opposition to EP Patent No. 1335987, Response, Aug. 9, 2010.
Martin Grund, Opposition to EP Patent No. 1335987, Response, Aug. 9, 2010.
Bavarian Nordic, Opposition to EP Patent No. 1335987, Response, Aug. 9, 2010.
Declaration of Dr. Dennis O. Chanter, Opposition to EP Patent No. 1335987, Aug. 6, 2010.
Declaration of Dr. Paul Chaplin, Opposition to EP Patent No. 1335987, Jul. 12, 2007.
Declaration of Dr. Paul Chaplin, Opposition to EP Patent No. 1335987, Jul. 25, 2007.
Declaration of Dr. Paul Chaplin, Opposition to EP Patent No. 1335987, Aug. 19, 2005.
Declaration of William D. Coston, Opposition to EP Patent No. 1335987, Jul. 15, 2010.
Declaration of Dr. Robert Drillien Opposition to EP Patent No. 1335987, Mar. 1, 2007.
Declaration of Dr. Falko-Gunter Falkner, Opposition to EP Patent No. 1335987, Aug. 5, 2010.
Declaration of Karl Heller, Opposition to EP Patent No. 1335987, Aug. 3, 2010.
Declaration of Dr. Bertram Jacobs, Opposition to EP Patent No. 1335987, Jul. 16, 2010.
Declaration of Dr. Paul Sharp, Opposition to EP Patent No. 1335987, Aug. 6, 2010.
Declaration of Dr. Leonard Shultz Opposition to EP Patent No. 1335987, Feb. 28, 2007.
Declaration of Niels Holger Wulff, Opposition to EP Patent No. 1335987, Jul. 25, 2007.
Asger Aamund, US Department of Health and Human Services awards an exclusive contract to Bavarian Nordic for the delivery of 20 million doses of IMVAMUNE. Financial guidance for 2007 is raised with DKK 300 million, Announcement No. 23-07, Bavarian Nordic, Jun. 4, 2007.
Ahmad et al., The SP-1 gene of Ravvitpox Virus Determines Host Range and Is Required for Hemorrhagic Pock Formation, Virology 202:305-314 (1994).
Altenburger et al., Partiaal Deletion of the human host range gene in the attenuated vaccinia virus MVA, Archives of Virology 105(1-2):15-27 (1989).
Asger Aamund, International Trade Commission Refers MVA Case Back to the Administrative Law Judge, Announcement No. 05-07, Bavarian Nordic, Feb. 22, 2007.
Aragane et al., Ultraviolet Light Induces Apoptosis via Direct Activation of CD95 (Fas/APO-1) Independently of Its Ligand CD95L, The Journal of Cell Biology, vol. 140, No. 1, Jan. 12, 1998 171-182.
Laurie Barclay, Center Watch—Eye on Sexually Transmitted Diseases, Aug. 2005.
Exposito et al., Vaccinia Virus strain Acambis 3000 Modified Virus Ankara (MVA) complete genome, AY603355, Genebank, Apr. 19, 2004.
The Jackson Laboratory, Description, Mouse Strain B6.CB17-Prkdcscid/SzJ, printed Apr. 27, 2010.
Asger Aamund, Annual Report 1997, Bavarian Nordic, Mar. 31, 1998.

Asger Aamund, Annual Report 1998, Bavarian Nordic, Mar. 25, 1999.
Asger Aamund, Annual Report 1999, Bavarian Nordic, Mar. 14, 2000.
Asger Aamund, Annual Report 2000, Bavarian Nordic, Mar. 16, 2001.
Bavarian Nordic Research Institute A/S, Company Profile, 1996.
Asger Aamund, European patent issued to Bavarian Nordic A/S on MVA-BN, Announcement No. 37-05, Bavarian Nordic, Dec. 28, 2005.
Bavarian Nordic Research Institute A/S, Prospectus, Nov. 2, 1998.
Dr. Petra Pielken, Response to Communication, European Patent Application No. 97 943 887.6-1212, Jun. 28, 2005.
Bavarian Nordic Website, Intellectual Property Rights, Printed Sep. 23, 2006.
Bosma et al., The SCID mouse mutant: definition, characterization, and potential uses, Ann. Rev Immunology 1991; 9:323-50 (Abstract).
Boukamp et al., Normal Keratinization in a Spontaneously Immortalized Aneuploid Human Keratinocyte Cell Line, The Journal of Cell Biology 106:761-771 (1988).
Dinicola et al., Immunization of Patients with Malignant Melanoma with Autologous CD34+ Cell-Derived Dendritic Cells Transduced Ex Vivo with a Recombinant Replication-Deficient Vaccinia vector Encoding the Human Tyrosinase Gene: A phase I Trial, Human Gene Therapy 14:1347-1360 (2003).
Drexler et al., Modified Vaccinia Virus Ankara for Delivery of Human Tyrosinase as Melanomaassociated Antigen: Induction of Tyrosinase- and Melanoma-specific HumanLeukocyte Antigen A*0201-restricted Cytotoxic T Cells in Vitro and in Vivo, Cancer Research 59, 4955-4963, Oct. 1, 1999.
Richard Condit, Principles of Virology, In Fields Virology (4th Ed), Knipe and Howley (Eds.), Lippincott Willams & Wilkins (2001), p. 21-51.
Hirsch et al., Patterns of viral replication correlate with outcome in simian immunodeficiency virus (SIV)-infected macaques: effect of prior immunization with a trivalent SIV vaccine in modified vaccinia virus Ankara, J Virol. Jun. 1996;70(6):3741-52.
Jackson et al., The p47phox Mouse Knock-Out Model of Chronic Granulomatous Disease, J. Experimental Medicine 182: 751-758 (1991).
Taconic Library, Leakiness in C.B-17 SCID vs. ICR SCID, printed Apr. 27, 2010.
Mayr and Danner, Vaccination against pox diseases under immunosuppressive conditions, Develop. Biol. Srandard 41:225-234 (1978).
Meyer et al., A phase I vacination study with tyrosinase in patients with stage II melanoma using recombinant modified virus Ankara (MVA-hTyr), Cancer Immunol Immunother 54:453-467 (2005).
Pilcher et al., The Activity of Collagenase-1 Is Required for Keratinocyte Migration on a Type I Collagen Matrix, The Journal of Cell Biology, vol. 137, No. 6, Jun. 16, 1997 1445-1457.
Ramirez et al., Attenuated Modified Vaccinia Virus Ankara Can Be Used as an Immunizing Agent under Conditions of Preexisting Immunity to the Vector, Journal of Virology 74:7651-7655 (2000).
Karl Heller, VIVACS Final Report, Analysis of different strains of Modiifed Vaccinia virus Ankara (MVA) regarding their capability to grow and replicate in various cell lines., Project #1200104, VIVACS GmbH, Martinsried, Germany, Jun. 29, 2005.
Rosenwirth et al., An anti-HIV strategy combining chemotherapy and therapeutic vaccination, J. Med. Primatol. 28:195-205 (1999.).
Spertzel et al., response of Irradiated Mice to Live Virus (TC-83) Immunization, Infection and Immunity 11:481-487 (1975).
Staib et al., Live Viral Vectors: Vaccinia Virus, In Methods in Molecular Medicine, vol. 87: Vaccine Protocols, 2nd ed. Edited by Robinson et al., Hunana Press Inc., Totowa, NJ (2003).
Stickl et al., Primary Vaccination Against Smallpox, Munch. Med. Wschr. 115, Nr 35. 1471-1473 (1973).
Stickl et al., MVA Vaccination Against Smallpox, Dtsch. med. Wschr. 99: 2386-2392 (1974).
Stittelar et al., Safety of modified vaccinia virus Ankara (MVA) in immune-suppressed macaques, Vaccine 19:3700-3709 (2001).
Volmar et al., Safety and immunogenicity of IMVAMUNE, a promising candidate as a third generation smallpox vaccine, Vaccine 24 (2006) 2065-2070.
Wyatt et al., Marker Rescue of Host Range Restriction Defects of Modified Vaccinia Virus Ankara, Virology 251:334-342 (1998).

* cited by examiner

A

B

MODIFIED VACCINIA ANKARA VIRUS VARIANT

The present invention provides an attenuated virus which is derived from Modified Vaccinia Ankara virus and which is characterized by the loss of its capability to reproductively replicate in human cell lines. It further describes recombinant viruses derived from this virus and the use of the virus or its recombinants as a medicament or vaccine. Additionally, a method is provided for inducing an immune response even in immune-compromised patients, patients with pre-existing immunity to the vaccine virus, or patients undergoing antiviral therapy.

BACKGROUND OF THE INVENTION

Modified Vaccinia Ankara (MVA) virus is related to vaccinia virus, a member of the genera Orthopoxvirus in the family of Poxyiridae. MVA was generated by 516 serial passages on chicken embryo fibroblasts of the Ankara strain of vaccinia virus (CVA) (for review see Mayr, A., et al. Infection 3, 6-14 [1975]). As a consequence of these long-term passages, the resulting MVA virus deleted about 31 kilobases of its genomic sequence and, therefore, was described as highly host cell restricted to avian cells (Meyer, H. et al., J. Gen. Virol. 72, 1031-1038 [1991]). It was shown in a variety of animal models that the resulting MVA was significantly avirulent (Mayr, A. & Danner, K. [1978] Dev. Biol. Stand. 41: 225-34). Additionally, this MVA strain has been tested in clinical trials as a vaccine to immunize against the human smallpox disease (Mayr et al., Zbl. Bakt. Hyg. I, Abt. Org. B 167, 375-390 [1987], Stickl et al., Dtsch. med. Wschr. 99, 2386-2392 [1974]). These studies involved over 120,000 humans, including high-risk patients, and proved that compared to vaccinia based vaccines, MVA had diminished virulence or infectiousness while it induced a good specific immune response.

In the following decades, MVA was engineered for use as a viral vector for recombinant gene expression or as a recombinant vaccine (Sutter, G. et al., [1994], Vaccine 12: 1032-40).

In this respect, it is most astonishing that even though Mayr et al. demonstrated during the 1970s that MVA is highly attenuated and avirulent in humans and mammals, some recently reported observations (Blanchard et al., 1998, J Gen Virol 79, 1159-1167; Carroll & Moss, 1997, Virology 238, 198-211; Altenberger, U.S. Pat. No. 5,185,146; Ambrosini et al., 1999, J Neurosci Res 55(5), 569) have shown that MVA is not fully attenuated in mammalian and human cell lines since residual replication might occur in these cells. It is assumed that the results reported in these publications have been obtained with various known strains of MVA since the viruses used essentially differ in their properties, particularly in their growth behavior in various cell lines.

Growth behavior is recognized as an indicator for virus attenuation. Generally, a virus strain is regarded as attenuated if it has lost its capacity or only has reduced capacity to reproductively replicate in host cells. The above-mentioned observation, that MVA is not completely replication incompetent in human and mammalian cells, brings into question the absolute safety of known MVA as a human vaccine or a vector for recombinant vaccines.

Particularly for a vaccine, as well as for a recombinant vaccine, the balance between the efficacy and the safety of the vaccine vector virus is extremely important.

OBJECT OF THE INVENTION

Thus, an object of the invention is to provide novel virus strains having enhanced safety for the development of safer products, such as vaccines or pharmaceuticals. Moreover, a further object is to provide a means for improving an existing vaccination regimen.

SUMMARY OF THE INVENTION

The invention inter alia comprises the following, alone or in combination:

A method for inducing an immune response for treating a human patient comprising:

(a) administering to the patient a priming inoculation of an effective amount of a MVA virus, wherein the MVA virus is characterized by reproductive replication in vitro in chicken embryo fibroblasts and by being non-replicative in vitro in human cell lines selected from the human keratinocyte cell line HaCaT, the human embryo kidney cell line 293, the human bone osteosarcoma cell line 143B, and the human cervix adenocarcinoma cell line HeLa; and (b) administering to the patient a boosting inoculation of an effective amount of a MVA virus, such a method wherein the MVA is MVA-BN as deposited at the European Collection of Cell Cultures (ECACC), Salisbury (UK) under number V00083008 or a derivative thereof, such a method wherein the MVA virus comprises a heterologous nucleic acid sequence, such a method wherein the heterologous nucleic acid sequence is selected from a sequence encoding at least one antigen, antigenic epitope, and/or a therapeutic compound, such a method wherein the antigen or antigenic epitope is derived from a virus selected from the family of Influenza virus, Flavivirus, Paramyxovirus, Hepatitis virus, Cytomegalovirus, Human immunodeficiency virus or from viruses causing hemorrhagic fever, such a method wherein the antigen or antigenic epitope comprises nef, such a method wherein an immune response is directed against HIV, such a method wherein the MVA virus is administered as a vaccine, such a method wherein the immune response is directed against an orthopox virus, selected from smallpox, such a method wherein the patient is immune compromised, such a method wherein the patient exhibits preexisting immunity to MVA, such a method wherein the MVA is administered by intravenous, intramuscular, and/or subcutaneous injection, such a method wherein the MVA prime/MVA boost inoculation regime induces at least the same level of immune response when compared to a DNA-prime/vaccinia virus boost inoculation regime, such a method wherein the MVA is administered at a dose of at least about $1 \times 10^8$ TCID$_{50}$, such a method wherein the priming inoculation MVA is administered about 4 weeks prior to the boosting inoculation MVA, such a method for inducing an immune response for treating a mammal comprising:

(a) administering to the mammal a priming inoculation of an effective amount of a MVA virus, wherein the MVA virus is characterized by reproductive replication in vitro in chicken embryo fibroblasts and by being non-replicative in vitro in human cell lines selected from the human keratinocyte cell line HaCaT, the human embryo kidney cell line 293, the human bone osteosarcoma cell line 143B, and the human cervix adenocarcinoma cell line HeLa; and (b) administering to the mammal a boosting inoculation of an effective amount of a MVA virus.

A kit for treating a human patient comprising:

(a) a MVA characterized by reproductive replication in vitro in chicken embryo fibroblasts and by being non-replicative in vitro in human cell lines selected from the human keratinocyte cell line HaCaT, the human embryo kidney cell line 293, the human bone osteosarcoma cell line 143B, and the human cervix adenocarcinoma cell line HeLa; and (b) instructions to administer the MVA in a priming inoculation and in a boosting inoculation, such a kit wherein the MVA is MVA-BN as deposited at the European Collection of Cell Cultures (ECACC), Salisbury (UK) under number V00083008 or a derivative thereof, such a kit wherein the MVA virus comprises a heterologous nucleic acid sequence, such a kit wherein the heterologous nucleic acid sequence is selected from a sequence encoding at least one antigen, antigenic epitope, and/or a therapeutic compound, such a kit wherein the antigen or antigenic epitope is derived from a virus selected from the family of Influenza virus, Flavivirus, Paramyxovirus, Hepatitis virus, Cytomegalovirus, Human immunodeficiency virus or from viruses causing hemorrhagic fever, such a kit wherein the MVA virus is administered as a vaccine, such a kit wherein the treatment is directed against an orthopox virus, selected from smallpox, such a kit wherein the treatment is directed to a patient who is immune compromised, such a kit wherein the MVA is administered by intravenous, intramuscular, and/or subcutaneous injection.

DETAILED DESCRIPTION OF THE INVENTION

To achieve the foregoing objectives, according to a preferred embodiment of the present invention, new vaccinia viruses are provided which are capable of reproductive replication in non-human cells and cell lines, especially in chicken embryo fibroblasts (CEF), but not capable of reproductive replication in a human cell line known to permit replication with known vaccinia strains.

Known vaccinia strains reproductively replicate in at least some human cell lines, in particular the human keratinocyte cell line HaCaT (Boukamp et al. 1988, J Cell Biol 106(3): 761-71). Replication in the HaCaT cell line is predictive for replication in vivo, in particular for in vivo replication in humans. It is demonstrated in the example section that all known vaccinia strains tested that show a residual reproductive replication in HaCaT also replicate in vivo. Thus, the invention preferably relates to vaccinia viruses that do not reproductively replicate in the human cell line HaCaT. Most preferably, the invention concerns vaccinia virus strains that are not capable of reproductive replication in any of the following human cell lines: human cervix adenocarcinoma cell line HeLa (ATCC No. CCL-2), human embryo kidney cell line 293 (ECACC No. 85120602), human bone osteosarcoma cell line 143B (ECACC No. 91112502) and the HaCaT cell line.

The growth behaviour or amplification/replication of a virus is normally expressed by the ratio of virus produced from an infected cell (Output) to the amount originally used to infect the cell in the first place (Input) ("amplification ratio"). A ratio of "1" between Output and Input defines an amplification status wherein the amount of virus produced from the infected cells is the same as the amount initially used to infect the cells. This ratio is understood to mean that the infected cells are permissive for virus infection and virus reproduction.

An amplification ratio of less than 1, i.e., a decrease of the amplification below input level, indicates a lack of reproductive replication and thus, attenuation of the virus. Therefore, it was of particular interest for the inventors to identify and isolate a strain that exhibits an amplification ratio of less than 1 in several human cell lines, in particular all of the human cell lines 143B, HeLa, 293, and HaCaT.

Thus, the term "not capable of reproductive replication" means that the virus of the present invention exhibits an amplification ratio of less than 1 in human cell lines, such as 293 (ECACC No. 85120602), 143B (ECACC No. 91112502), HeLa (ATCC No. CCL-2) and HaCaT (Boukamp et al. 1988, J Cell Biol 106(3): 761-71) under the conditions outlined in Example 1 of the present specification. Preferably, the amplification ratio of the virus of the invention is 0.8 or less in each of the above human cell lines, i.e., HeLa, HaCaT, and 143B.

Figure 1B:
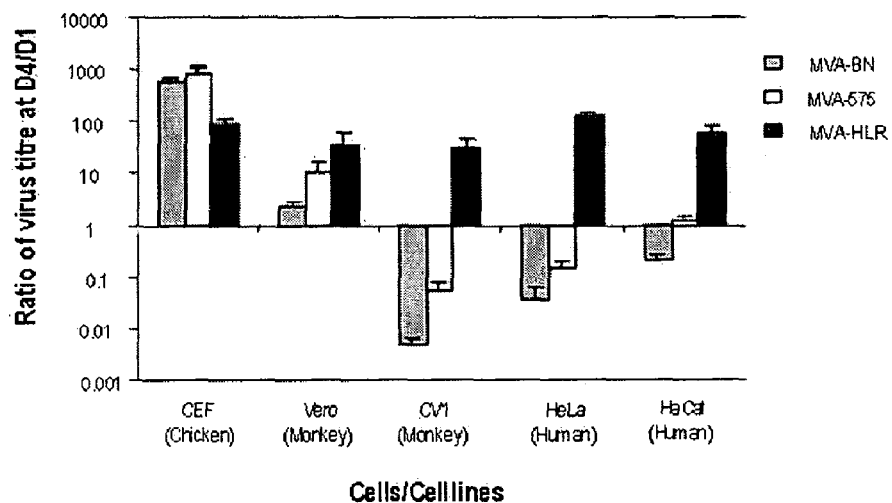

Viruses of the invention are demonstrated in Example 1 and Table 1 not to reproductively replicate in cell lines 143B, HeLa and HaCaT. The particular strain of the invention that has been used in the examples was deposited on Aug. 30, 2000 at the European Collection of Cell Cultures (ECACC) under number V00083008. This strain is referred to as "MVA-BN" throughout the Specification. It has already been noted that the known MVA strains show residual replication in at least one of the human cell lines tested (FIG. 1, Example 1). All known vaccinia strains show at least some replication in the cell line HaCaT, whereas the MVA strains of the invention, in particular MVA-BN, do not reproductively replicate in HaCaT cells. In particular, MVA-BN exhibits an amplification ratio of 0.05 to 0.2 in the human embryo kidney cell line 293 (ECACC No. 85120602). In the human bone osteosarcoma cell line 143B (ECACC No. 91112502), the ratio is in the range of 0.0 to 0.6. For the human cervix adenocarcinoma cell line HeLa (ATCC No. CCL-2) and the human keratinocyte cell line HaCaT (Boukamp et al. 1988, J Cell Biol 106(3): 761-71), the amplification ratio is in the range of 0.04 to 0.8 and of 0.02 to 0.8, respectively. MVA-BN has an amplification ratio of 0.01 to 0.06 in African green monkey kidney cells (CV1: ATCC No. CCL-70). Thus, MVA-BN, which is a representative strain of the invention, does not reproductively replicate in any of the human cell lines tested.

The amplification ratio of MVA-BN is clearly above 1 in chicken embryo fibroblasts (CEF: primary cultures). As outlined above, a ratio of more than "1" indicates reproductive replication since the amount of virus produced from the infected cells is increased compared to the amount of virus that was used to infect the cells. Therefore, the virus can be easily propagated and amplified in CEF primary cultures with a ratio above 500.

In a particular embodiment of the present invention, the invention concerns derivatives of the virus as deposited under ECACC V0083008. "Derivatives" of the viruses as deposited under ECACC V00083008 refer to viruses exhibiting essentially the same replication characteristics as the deposited strain but exhibiting differences in one or more parts of its genome. Viruses having the same "replication characteristics" as the deposited virus are viruses that replicate with similar amplification ratios as the deposited strain in CEF cells and the cell lines HeLa, HaCaT and 143B; and that show a similar replication in vivo, as determined in the AGR129 transgenic mouse model (see below).

In a further preferred embodiment, the vaccinia virus strains of the invention, in particular MVA-BN and its derivatives, are characterized by a failure to replicate in vivo. In the context of the present invention, "failure to replicate in vivo" refers to viruses that do not replicate in humans and in the mouse model described below. The "failure to replicate in vivo" can be preferably determined in mice that are incapable of producing mature B and T cells. An example of such mice is the transgenic mouse model AGR129 (obtained from Mark Sutter, Institute of Virology, University of Zurich, Zurich, Switzerland). This mouse strain has targeted gene disruptions in the IFN receptor type I (IFN-α/β) and type II (IFN-γ) genes, and in RAG. Due to these disruptions, the mice have no IFN system and are incapable of producing mature B and T cells, and as such, are severely immune-compromised and highly susceptible to a replicating virus. In addition to the AGR129 mice, any other mouse strain can be used that is incapable of producing mature B and T cells, and as such, is severely immune-compromised and highly susceptible to a replicating virus. In particular, the viruses of the present invention do not kill AGR129 mice within a time period of at least 45 days, more preferably within at least 60 days, and most preferably within 90 days post infection of the mice with $10^7$ pfu virus administered via intra-peritoneal injection. Preferably, the viruses that exhibit "failure to replicate in vivo" are further characterized in that no virus can be recovered from organs or tissues of the AGR129 mice 45 days, preferably 60 days, and most preferably 90 days after infection of the mice with $10^7$ pfu virus administered via intra-peritoneal injection. Detailed information regarding the infection assays using AGR129 mice and the assays used to determine whether virus can be recovered from organs and tissues of infected mice can be found in the example section.

In a further preferred embodiment, the vaccinia virus strains of the invention, in particular MVA-BN and its derivatives, are characterized as inducing a higher specific immune response compared to the strain MVA-575, as determined in a lethal challenge mouse model. Details of this experiment are outlined in Example 2, shown below. Briefly, in such a model unvaccinated mice die after infection with replication competent vaccinia strains such as the Western Reserve strain L929 TK+ or IHD-J. Infection with replication competent vaccinia viruses is referred to as "challenge" in the context of description of the lethal challenge model. Four days after the challenge, the mice are usually killed and the viral titre in the ovaries is determined by standard plaque assays using VERO cells (for more details see example section). The viral titre is determined for unvaccinated mice and for mice vaccinated with vaccina viruses of the present invention. More specifically, the viruses of the present invention are characterized in that, in this test after the vaccination with $10^2$ TCID$_{50}$/ml of virus of the present invention, the ovarian virus titres are reduced by at least 70%, preferably by at least 80%, and more preferably by at least 90%, compared to unvaccinated mice.

In a further preferred embodiment, the vaccinia viruses of the present invention, in particular MVA-BN and its derivatives, are useful for immunization with prime/boost administration of the vaccine. There have been numerous reports suggesting that prime/boost regimes using a known MVA as a delivery vector induce poor immune responses and are inferior to DNA-prime/MVA-boost regimes (Schneider et al., 1998, Nat. Med. 4; 397-402). In all of those studies the MVA strains that have been used are different from the vaccinia viruses of the present invention. To explain the poor immune response if MVA was used for prime and boost administration it has been hypothesized that antibodies generated to MVA during the prime-administration neutralize the MVA administered in the second immunization, thereby preventing an effective boost of the immune response. In contrast, DNA-prime/MVA-boost regimes are reported to be superior at generating high avidity responses because this regime combines the ability of DNA to effectively prime the immune response with the properties of MVA to boost the response in the absence of a pre-existing immunity to MVA. Clearly, if a pre-existing immunity to MVA and/or vaccinia prevents boosting of the immune response, then the use of MVA as a vaccine or therapeutic would have limited efficacy, particularly in the individuals that have been previously vaccinated against smallpox. However, according to a further embodiment, the vaccinia virus of the present invention, in particular MVA-BN and its derivatives, as well as corresponding recombinant viruses harboring heterologous sequences, can be used to efficiently first prime and then boost immune responses in naive animals, as well as animals with a pre-existing immunity to poxviruses. Thus, the vaccinia virus of the present invention induces at least substantially the same level of immunity in vaccinia virus prime/vaccinia virus boost regimes compared to DNA-prime/vaccinia virus boost regimes. The term "animal" as used in the present description is intended to also include human beings. Thus, the virus of the present invention is also useful for prime/boost regimes in human beings. If the virus is a non-recombinant virus such as MVA-BN or a derivative thereof, the virus may be used as a smallpox vaccine in humans, wherein the same virus can be used in both the priming and boosting vaccination. If the virus is a recombinant virus such as MVA-BN or a derivative thereof that encodes a heterologous antigen, the virus may be used in humans as a vaccine against the agent from which the heterologous antigen is derived, wherein the same virus can be used in both the priming and boosting vaccination.

A vaccinia virus is regarded as inducing at least substantially the same level of immunity in vaccinia virus prime/vaccinia virus boost regimes if, when compared to DNA-prime/vaccinia virus boost regimes, the CTL response, as measured in one of the following two assays ("assay 1" and "assay 2"), preferably in both assays, is at least substantially the same in vaccinia virus prime/vaccinia virus boost regimes when compared to DNA-prime/vaccinia virus boost regimes. More preferably, the CTL response after vaccinia virus prime/vaccinia virus boost administration is higher in at least one of the assays, when compared to DNA-prime/vaccinia virus boost regimes. Most preferably, the CTL response is higher in both of the following assays:

Assay 1: For vaccinia virus prime/vaccinia virus boost administrations, 6-8 week old BALB/c (H-2d) mice are prime-immunized by intravenous administration with $10^7$ TCID$_{50}$ vaccinia virus of the invention expressing the murine polytope as described in Thomson et al., 1998, J. Immunol. 160, 1717 and then boost-immunized with the same amount of the same virus, administered in the same manner three weeks later. To this end, it is necessary to construct a recombinant vaccinia virus expressing the polytope. Methods to construct such recombinant viruses are known to a person skilled in the art and are described in more detail below. In DNA prime/vaccinia virus boost regimes the prime vaccination is done by intra muscular injection of the mice with 50 μg DNA expressing the same antigen as the vaccinia virus. The boost administration with the vaccinia virus is done in exactly the same way as for the vaccinia virus prime/vaccinia virus boost administration. The DNA plasmid expressing the polytope is also described in the publication referenced above, i.e., Thomson, et al. In both regimes, the development of a CTL response against the epitopes SYI, RPQ and/or YPH is determined two weeks after the boost administration. The determination of the CTL response is preferably done using the ELISPOT analysis as described by Schneider, et al., 1998, Nat. Med. 4, 397-402, and as outlined in the examples section below for a specific virus of the invention. The virus of the invention is characterized in this experiment in that the CTL immune response against the epitopes mentioned above, which is induced by the vaccinia virus prime/vaccinia virus boost administration, is substantially the same, preferably at least the same, as that induced by DNA prime/vaccinia virus boost administration, as assessed by the number of IFN-γ producing cells/$10^6$ spleen cells (see also experimental section).

Assay 2: This assay basically corresponds to assay 1. However, instead of using $10^7$ TCID$_{50}$ vaccinia virus administered i.v., as in Assay 1; in Assay 2, $10^8$ TCID$_{50}$ vaccinia virus of the present invention is administered by subcutaneous injection for both prime and boost immunization. The virus of the present invention is characterized in this experiment in that the CTL immune response against the epitopes mentioned above, which is induced by the vaccinia virus prime/vaccinia virus boost administration, is substantially the same, preferably at least the same, as that induced by DNA prime/vaccinia virus boost administration, as assessed by the number of IFN-γ producing cells/$10^6$ spleen cells (see also experimental section).

The strength of a CTL response as measured in one of the assays shown above corresponds to the level of protection.

Thus, the viruses of the present invention are particularly suitable for vaccination purposes.

In summary, a representative vaccinia virus of the present invention is characterized by having at least one of the following properties:
 (i) capability of reproductive replication in chicken embryo fibroblasts (CEF), but no capability of reproductive replication in a human cell line known to permit replication with known vaccinia strains,
 (ii) failure to replicate in vivo in those animals, including humans, in which the virus is used as a vaccine or active ingredient of a pharmaceutical composition,
 (iii) induction of a higher specific immune response compared to a known vaccinia strain and/or
 (iv) induction of at least substantially the same level of a specific immune response in vaccinia virus prime/vaccinia virus boost regimes when compared to DNA-prime/vaccinia virus boost regimes.

Preferably, the vaccinia virus of the present invention has at least two of the above properties, and more preferably at least three of the above properties. Most preferred are vaccinia viruses having all of the above properties.

Representative vaccinia virus strains are MVA-575 deposited on Dec. 7, 2000 at the European Collection of Animal Cell Cultures (ECACC) with the deposition number V00120707; and MVA-BN, deposited on Aug. 30, 2000, at ECACC with the deposition number V000083008, and derivatives thereof, in particular if it is intended to vaccinate/treat humans. MVA-BN and its derivatives are most preferred for humans.

In a further embodiment, the invention concerns a kit for vaccination comprising a virus of the present invention for the first vaccination ("priming") in a first vial/container and for a second vaccination ("boosting") in a second vial/container. The virus may be a non-recombinant vaccinia virus, i.e., a vaccinia virus that does not contain heterologous nucleotide sequences. An example of such a vaccinia virus is MVA-BN and its derivatives. Alternatively, the virus may be a recombinant vaccinia virus that contains additional nucleotide sequences that are heterologous to the vaccinia virus. As outlined in other sections of the description, the heterologous sequences may code for epitopes that induce a response by the immune system. Thus, it is possible to use the recombinant vaccinia virus to vaccinate against the proteins or agents comprising the epitope. The viruses may be formulated as shown below in more detail. The amount of virus that may be used for each vaccination has been defined above.

A process to obtain a virus of the instant invention may comprise the following steps:
 (i) introducing a vaccinia virus strain, for example MVA-574 or MVA-575 (ECACC V00120707) into non-human cells in which the virus is able to reproductively replicate, wherein the non-human cells are preferably selected from CEF cells,
 (ii) isolating/enriching virus particles from these cells and
 (iii) analyzing whether the obtained virus has at least one of the desired biological properties as previously defined above, wherein the above steps can optionally be repeated until a virus with the desired replication characteristics is obtained. The invention further relates to the viruses obtained by the method of the instant invention. Methods for determining the expression of the desired biological properties are explained in other parts of this description.

In applying this method, a strain of the present invention may be identified and isolated which corresponds to the strain with the accession number ECACC V0083008, mentioned above.

The growth behavior of the vaccinia viruses of the present invention, in particular the growth behavior of MVA-BN, indicates that the strains of the present invention are far superior to any other characterized MVA isolates in terms of attenuation in human cell lines and failure to replicate in vivo. The strains of the present invention are therefore ideal candidates for the development of safer products such as vaccines or pharmaceuticals, as described below.

In one further embodiment, the virus of the present invention, in particular MVA-BN and its derivatives, is used as a vaccine against human poxvirus diseases, such as smallpox.

In a further embodiment, the virus of the present invention may be recombinant, i.e., may express heterologous genes as, e.g., antigens or epitopes heterologous to the virus, and may thus be useful as a vaccine to induce an immune response against heterologous antigens or epitopes.

The term "immune response" means the reaction of the immune system when a foreign substance or microorganism enters the organism. By definition, the immune response is divided into a specific and an unspecific reaction although both are closely related. The unspecific immune response is the immediate defence against a wide variety of foreign substances and infectious agents. The specific immune response is the defence raised after a lag phase, when the organism is challenged with a substance for the first time. The specific immune response is highly efficient and is responsible for the fact that an individual who recovers from a specific infection is protected against this specific infection. Thus, a second infection with the same or a very similar infectious agent causes much milder symptoms or no symptoms at all, since there is already a "pre-existing immunity" to this agent. Such immunity and immunological memory persist for a long time, in some cases even lifelong. Accordingly, the induction of an immunological memory can be used for vaccination.

The "immune system" means a complex organ involved in the defence of the organism against foreign substances and microorganisms. The immune system comprises a cellular component, comprising several cell types, such as, e.g., lymphocytes and other cells derived from white blood cells, and a humoral component, comprising small peptides and complement factors.

"Vaccination" means that an organism is challenged with an infectious agent, e.g., an attenuated or inactivated form of the infectious agent, to induce a specific immunity. The term vaccination also covers the challenge of an organism with recombinant vaccinia viruses of the present invention, in particular recombinant MVA-BN and its derivatives, expressing antigens or epitopes that are heterologous to the virus. Examples of such epitopes are provided elsewhere in the description and include e.g., epitopes from proteins derived from other viruses, such as the Dengue virus, Hepatitis C virus, HIV, or epitopes derived from proteins that are associated with the development of tumors and cancer. Following administration of the recombinant vaccinia virus, the epitopes are expressed and presented to the immune system. A specific immune response against these epitopes may be induced. The organism, thus, is immunized against the agent/protein containing the epitope that is encoded by the recombinant vaccinia virus.

"Immunity" means partial or complete protection of an organism against diseases caused by an infectious agent due to a successful elimination of a preceding infection with the infectious agent or a characteristic part thereof. Immunity is based on the existence, induction, and activation of specialized cells of the immune system.

As indicated above, in one embodiment of the invention the recombinant viruses of the present invention, in particular recombinant MVA-BN and its derivatives, contain at least one heterologous nucleic acid sequence. The term "heterologous" is used hereinafter for any combination of nucleic acid sequences that is not normally found intimately associated with the virus in nature; such virus is also called a "recombinant virus".

According to a further embodiment of the present invention, the heterologous sequences are preferably antigenic epitopes that are selected from any non-vaccinia source. Most preferably, the recombinant virus expresses one or more antigenic epitopes from: *Plasmodium falciparum,* mycobacteria, influenza virus, viruses of the family of flaviviruses, paramyxoviruses, hepatitis viruses, human immunodeficiency viruses, or from viruses causing hemorrhagic fever, such as hantaviruses or filoviruses, i.e., ebola or marburg virus.

According to still a further embodiment, but also in addition to the above-mentioned selection of antigenic epitopes, the heterologous sequences can be selected from another poxviral or a vaccinia source. These viral sequences can be used to modify the host spectrum or the immunogenicity of the virus.

In a further embodiment the virus of the present invention may code for a heterologous gene/nucleic acid expressing a therapeutic compound. A "therapeutic compound" encoded by the heterologous nucleic acid in the virus can be, e.g., a therapeutic nucleic acid, such as an antisense nucleic acid or a peptide or protein with desired biological activity.

According to a further preferred embodiment, the expression of a heterologous nucleic acid sequence is preferably, but not exclusively, under the transcriptional control of a poxvirus promoter, more preferably of a vaccinia virus promoter.

According to still a further embodiment, the heterologous nucleic acid sequence is preferably inserted into a non-essential region of the virus genome. In another preferred embodiment of the invention, the heterologous nucleic acid sequence is inserted at a naturally occurring deletion site of the MVA genome as disclosed in PCT/EP96/02926. Methods for inserting heterologous sequences into the poxviral genome are known to a person skilled in the art.

According to yet another preferred embodiment, the invention also includes the genome of the virus, its recombinants, or functional parts thereof. Such viral sequences can be used to identify or isolate the virus or its recombinants, e.g., by using PCR, hybridization technologies, or by establishing ELISA assays. Furthermore, such viral sequences can be expressed from an expression vector to produce the encoded protein or peptide that then may supplement deletion mutants of a virus that lacks the viral sequence contained in the expression vector.

"Functional part" of the viral genome means a part of the complete genomic sequence that encodes a physical entity, such as a protein, protein domain, or an epitope of a protein. Functional part of the viral genome also describes parts of the complete genomic sequence that code for regulatory elements or parts of such elements with individualized activity, such as promoter, enhancer, cis- or trans-acting elements.

The recombinant virus of the present invention may be used for the introduction of a heterologous nucleic acid sequence into a target cell, the sequence being either homologous or heterologous to the target cell. The introduction of a heterologous nucleic acid sequence into a target cell may be used to produce in vitro heterologous peptides or polypeptides, and/or complete viruses encoded by the sequence. This method comprises the infection of a host cell with the recombinant MVA; cultivation of the infected host cell under suitable conditions; and isolation and/or enrichment of the peptide, protein and/or virus produced by the host cell.

Furthermore, the method for introduction of a homologous or heterologous sequence into cells may be applied for in vitro and preferably in vivo therapy. For in vitro therapy, isolated cells that have been previously (ex vivo) infected with the virus are administered to a living animal body for inducing an immune response. For in vivo therapy, the virus or its recombinants are directly administered to a living animal body to induce an immune response. In this case, the cells surrounding the site of inoculation are directly infected in vivo by the virus, or its recombinants, of the present invention.

Since the virus of the invention is highly growth restricted in human and monkey cells and thus, highly attenuated, it is ideal to treat a wide range of mammals, including humans. Hence, the present invention also provides a pharmaceutical composition and a vaccine, e.g., for inducing an immune response in a living animal body, including a human. The virus of the invention is also safe in any other gene therapy protocol.

The pharmaceutical composition may generally include one or more pharmaceutical acceptable and/or approved carriers, additives, antibiotics, preservatives, adjuvants, diluents and/or stabilizers. Such auxiliary substances can be water, saline, glycerol, ethanol, wetting or emulsifying agents, pH buffering substances, or the like. Suitable carriers are typically large, slowly metabolized molecules such as proteins, polysaccharides, polylactic acids, polyglycolic acids, polymeric amino acids, amino acid copolymers, lipid aggregates, or the like.

For the preparation of vaccines, the virus or a recombinant of the present invention, is converted into a physiologically acceptable form. This can be done based on experience in the preparation of poxvirus vaccines used for vaccination against smallpox (as described by Stickl, H. et al. [1974] Dtsch. med. Wschr. 99, 2386-2392). For example, the purified virus is stored at −80° C. with a titre of $5 \times 10^8$ TCID$_{50}$/ml formulated in about 10 mM Tris, 140 mM NaCl, pH 7.4. For the preparation of vaccine shots, e.g., $10^2$-$10^8$ particles of the virus are lyophilized in 100 ml of phosphate-buffered saline (PBS) in the presence of 2% peptone and 1% human albumin in an ampoule, preferably a glass ampoule. Alternatively, the vaccine shots can be produced by stepwise, freeze-drying of the virus in a formulation. This formulation can contain additional additives such as mannitol, dextran, sugar, glycine, lactose, polyvinylpyrrolidone, or other additives, such as antioxidants or inert gas, stabilizers or recombinant proteins (e.g. human serum albumin) suitable for in vivo administration. The glass ampoule is then sealed and can be stored between 4° C. and room temperature for several months. However, as long as no need exists the ampoule is stored preferably at temperatures below −20° C.

For vaccination or therapy, the lyophilisate can be dissolved in 0.1 to 0.5 ml of an aqueous solution, preferably physiological saline or Tris buffer, and administered either systemically or locally, i.e., by parenteral, intramuscular, or any other path of administration know to a skilled practitioner. The mode of administration, dose, and number of administrations can be optimized by those skilled in the art in a known manner.

Additionally according to a further embodiment, the virus of the present invention is particularly useful to induce immune responses in immune-compromised animals, e.g., monkeys (CD4<400/μl of blood) infected with SIV, or immune-compromised humans. The term "immune-compromised" describes the status of the immune system of an individual that exhibits only incomplete immune responses or has a reduced efficiency in the defence against infectious agents. Even more interesting and according to still a further embodiment, the virus of the present invention can boost immune responses in immune-compromised animals or humans even in the presence of a pre-existing immunity to poxvirus in these animals or humans. Of particular interest, the virus of the present invention can also boost immune responses in animals or humans receiving an antiviral, e.g., antiretroviral therapy. "Antiviral therapy" includes therapeutic concepts in order to eliminate or suppress viral infection including, e.g., (i) the administration of nucleotide analogs, (ii) the administration of inhibitors for viral enzymatic activity or viral assembling, or (iii) the administration of cytokines to influence immune responses of the host.

According to still a further embodiment, the vaccine is especially, but not exclusively, applicable in the veterinary field, e.g., immunization against animal pox infection. In small animals, the immunizing inoculation is preferably administered by nasal or parenteral administration, whereas in larger animals or humans, a subcutaneous, oral, or intramuscular inoculation is preferred.

The inventors have found that a vaccine shot containing an effective dose of only $10^2$ $TCID_{50}$ (tissue culture infectious dose) of the virus of the present invention is sufficient to induce complete immunity against a wild type vaccinia virus challenge in mice. This is particularly surprising since such a high degree of attenuation of the virus of the present invention would be expected to negatively influence and thereby, reduce its immunogenicity. Such expectation is based on the understanding that for induction of an immune response, the antigenic epitopes must be presented to the immune system in sufficient quantity. A virus that is highly attenuated and thus, not replicating, can only present a very small amount of antigenic epitopes, i.e., as much as the virus itself incorporates. The amount of antigen carried by viral particles is not considered to be sufficient for induction of a potent immune response. However, the virus of the invention stimulates, even with a very low effective dose of only $10^2$ $TCID_{50}$, a potent and protective immune response in a mouse/vaccinia challenge model. Thus, the virus of the present invention exhibits an unexpected and increased induction of specific immunity compared to other characterized MVA strains. This makes the virus of the present invention and any vaccine derived thereof, especially useful for application in immune-compromised animals or humans.

According to still another embodiment of the invention, the virus is used as an adjuvant. An "adjuvant" in the context of the present description refers to an enhancer of the specific immune response in vaccines. "Using the virus as adjuvant" means including the virus in a pre-existing vaccine to additionally stimulate the immune system of the patient who receives the vaccine. The immunizing effect of an antigenic epitope in most vaccines is often enhanced by the addition of a so-called adjuvant. An adjuvant co-stimulates the immune system by causing a stronger specific immune reaction against an antigenic epitope of a vaccine. This stimulation can be regulated by factors of the unspecific immune system, such as interferon and interleukin. Hence, in a further embodiment of the invention, the virus is used in mammals, including humans, to activate, support, or suppress the immune system, and preferably to activate the immune response against any antigenic determinant. The virus may also be used to support the immune system in a situation of increased susceptibility to infection, such as in the case of stress.

The virus used as an adjuvant may be a non-recombinant virus, i.e., a virus that does not contain heterologous DNA in its genome. An example of this type of virus is MVA-BN. Alternatively, the virus used as an adjuvant is a recombinant virus containing in its genome heterologous DNA sequences that are not naturally present in the viral genome. For use as an adjuvant, the recombinant viral DNA preferably contains and expresses genes that code for immune stimulatory peptides or proteins such as interleukins.

According to a further embodiment, it is preferred that the virus is inactivated when used as an adjuvant or added to another vaccine. The inactivation of the virus may be performed by e.g., heat or chemicals, as known in the art. Preferably, the virus is inactivated by β-propriolacton. According to this embodiment of the invention, the inactivated virus may be added to vaccines against numerous infectious or proliferative diseases to increase the immune response of the patient to this disease.

BRIEF DESCRIPTION OF THE FIGURES

FIG. 1: Growth kinetics of different strains of MVA in different cell lines. In 1A, the results are grouped according to the MVA strains tested; whereas in 1B, the results are grouped according to the cell lines tested. In 1B, the amount of virus recovered from a cell line after four days (D4) of culture was determined by plaque assay and expressed as the ratio of virus recovered after 4 days to the initial inoculum on day 1 (D1).

FIG. 2: Protection provided against a lethal challenge of vaccinia following vaccinations with either MVA-BN or MVA-575. The protection is measured by the reduction in ovarian titres determined 4 days post challenge by standard plaque assay.

FIG. 3: Induction of CTL and protection provided against an influenza challenge using different prime/boost regimes. 3A: Induction of CTL responses to 4 different H-2d restricted epitopes following vaccination with different combinations of DNA or MVA-BN vaccines encoding a murine polytope. BALB/c mice (5 per group) were vaccinated with either DNA (intramuscular) or MVA-BN (subcutaneous) and received booster immunizations three weeks later. CTL responses to 4 different epitopes encoded by the vaccines (TYQ, infuenza;

SYI, *P. berghei*; YPH, cytomegalovirus; RPQ, LCV) were determined using an ELISPOT assay 2 weeks post booster immunizations.

3B: Induction of CTL responses to 4 different epitopes following vaccination with different combinations of DNA or MVA-BN vaccines encoding a murine polytope. BALB/c mice (5 per group) were vaccinated with either DNA (intramuscular) or MVA-BN (intraveneous) and received booster immunizations three weeks later. CTL responses to 4 different epitopes encoded by the vaccines (TYQ, influenza; SYI, *P. berghei*; YPH, cytomegalovirus; RPQ, LCV) were determined using an ELISPOT assay 2 weeks post booster immunizations.

3C: Frequency of peptide and MVA specific T cells following homologous prime/boost using an optimal dose ($1 \times 10^8$ $TCID_{50}$) of recombinant MVA-BN, administered subcutaneous. Groups of 8 mice were vaccinated with two shots of the combinations as indicated in the figure. Two weeks after the final vaccination, peptide-specific splenocytes were enumerated using an IFN-gamma ELISPOT assay. The bars represent the mean number of specific spots plus/minus the standard deviation from the mean.

Figure 4:
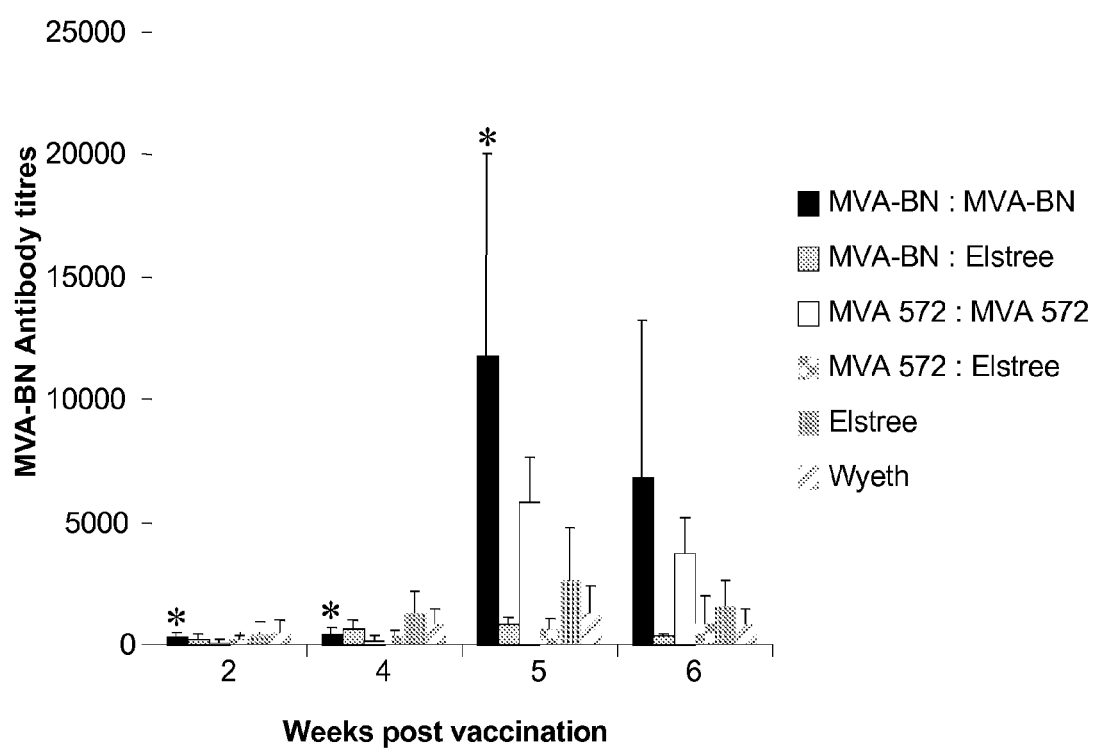

FIG. 4: Induction of antibodies to MVA following vaccination of mice with different smallpox vaccines. The levels of antibodies generated to MVA following vaccination with MVA-BN (week 0 and 4), was compared to conventional vaccinia strains, Elstree and Wyeth, given via tail scarification (week 0), MVA-572 (week 0 and 4), and MVA-BN and MVA-572 given as a pre-Elstree vaccine. MVA-572 has been deposited at the European Collection of Animal Cell Cultures as ECACC V94012707. The titres were determined using a capture ELISA and calculated by linear regression using the linear part of the graph and defined as the dilution that resulted in an optical density of 0.3.*MVA-BN: MVA-BN is significantly ($p>0.05$) different to MVA-572: MVA-572.

EXAMPLES

The following examples further illustrate the present invention. It should be understood by a person skilled in the art that the examples may not be interpreted in any way to limit the applicability of the technology provided by the present invention to specific application in these examples.

Example 1

Growth Kinetics of a New Strain of MVA in Selected Cell Lines and Replication In Vivo (1.1) Growth Kinetics in Cell Lines:

To characterize a newly isolated strain of the present invention (further referred to as MVA-BN) the growth kinetics of the new strain were compared to those of known MVA strains that have already been characterized.

The experiment compared the growth kinetics of the following viruses in the subsequently listed primary cells and cell lines:

MVA-BN (Virus stock #23, 18. 02. 99 crude, titered at $2.0 \times 10^7$ $TCID_{50}$/ml);

MVA as characterized by Altenburger (U.S. Pat. No. 5,185,146) and further referred to as MVA-HLR;

MVA (passage 575) as characterized by Anton Mayr (Mayr, A., et al. [1975] Infection 3; 6-14) and further referred to as MVA-575 (ECACC V00120707); and MVA-Vero as characterized in the International Patent Application PCT/EP01/02703 (WO 01/68820); Virus stock, passage 49, #20, 22.03.99 crude, titered at $4.2 \times 10^7$ $TCID_{50}$/ml.

The primary cells and cell lines used were:

| | |
|---|---|
| CEF | Chicken embryo fibroblasts (freshly prepared from SPF eggs); |
| HeLa | Human cervix adenocarcinoma (epithelial), ATCC No. CCL-2; |
| 143B | Human bone osteosarcoma TK-, ECACC No. 91112502; |
| HaCaT | Human keratinocyte cell line, Boukamp et al. 1988, J Cell Biol 106(3): 761-771; |
| BHK | Baby hamster kidney, ECACC 85011433; |
| Vero | African green monkey kidney fibroblasts, ECACC 85020299; |
| CV1 | African green monkey kidney fibroblasts, ECACC 87032605. |

For infection the cells were seeded onto 6-well-plates at a concentration of $5 \times 10^5$ cells/well and incubated overnight at 37° C., 5% $CO_2$ in DMEM (Gibco, Cat. No. 61965-026) with 2% FCS. The cell culture medium was removed and cells were infected at approximately moi 0.05 for one hour at 37° C., 5% $CO_2$ (for infection it is assumed that cell numbers doubled over night). The amount of virus used for each infection was $5 \times 10^4$ $TCID_{50}$ and is referred to as Input. The cells were then washed 3 times with DMEM and finally 1 ml DMEM, 2% FCS was added and the plates were left to incubate for 96 hours (4 days) at 37° C., 5% $CO_2$. The infections were stopped by freezing the plates at –80° C.; followed by titration analysis.

Titration Analysis (Immunostaining with a Vaccinia Virus Specific Antibody)

For titration of amount of virus test cells (CEF) were seeded on 96-well-plates in RPMI (Gibco, Cat. No. 61870-010), 7% FCS, 1% Antibiotic/Antimycotic (Gibco, Cat. No. 15240-062) at a concentration of $1 \times 10^4$ cells/well and incubated over night at 37° C., 5% $CO_2$. The 6-well-plates containing the infection experiments were frozen/thawed 3 times and dilutions of $10^{-1}$ to $10^{-12}$ were prepared using RPMI growth medium. Virus dilutions were distributed onto test cells and incubated for five days at 37° C., 5% $CO_2$ to allow CPE (cytopathic effect) development. Test cells were fixed (Acetone/Methanol 1:1) for 10 min, washed with PBS and incubated with polyclonal vaccinia virus specific antibody (Quartett Berlin, Cat. No. 9503-2057) at a 1:1000 dilution in incubation buffer for one hour at RT. After washing twice with PBS (Gibco, Cat. No. 20012-019) the HRP-coupled anti-rabbit antibody (Promega Mannheim, Cat. No. W4011) was added at a 1:1000 dilution in incubation buffer (PBS containing 3% FCS) for one hour at RT. Cells were again washed twice with PBS and incubated with staining solution (10 ml PBS+200 µl saturated solution of o-dianisidine in 100% ethanol +15 µl $H_2O_2$ freshly prepared) until brown spots were visible (two hours). Staining solution was removed and PBS was added to stop the staining reaction. Every well exhibiting a brown spot was marked as positive for CPE and the titre was calculated using the formula of Kaerber ($TCID_{50}$ based assay) (Kaerber, G. 1931. Arch. Exp. Pathol. Pharmakol. 162, 480).

The viruses were used to infect duplicate sets of cells that were expected to be permissive for MVA (i.e., CEF and BHK) and cells expected to be non-permissive for MVA (i.e., CV-1, Vero, HeLa, 143B and HaCaT). The cells were infected at a low multiplicity of infection, i.e., 0.05 infectious units per cell ($5 \times 10^4$ $TCID_{50}$). The virus inoculum was removed and the cells were washed three times to remove any remaining unabsorbed viruses. Infections were left for a total of 4 days when viral extracts were prepared and then titered on CEF cells.

Table 1 and FIG. 1 show the results of the titration assays where values are given as total amount of virus produced after 4 days infection.

It was demonstrated that all viruses amplified well in CEF cells as expected, since this is a permissive cell line for all MVAs. Additionally, it was demonstrated that all viruses amplified well in BHK (Hamster kidney cell line). MVA-Vero performed the best, since BHK is a permissive cell line for this strain.

Concerning replication in Vero cells (Monkey kidney cell line), MVA-Vero amplified well, as expected, i.e., 1000 fold above Input. MVA-HLR and also MVA-575 amplified well with a 33-fold and 10-fold increase above Input, respectively. Only MVA-BN was found to not amplify as well in these cells when compared to the other strains, i.e., only a 2-fold increase above Input.

Also concerning replication in CV1 cells (Monkey kidney cell line), it was found that MVA-BN is highly attenuated in this cell line. It exhibited a 200-fold decrease below Input. MVA-575 did not amplify above the Input level and also exhibited a slight negative amplification, i.e., 16-fold decrease below Input. MVA-HLR amplified the best with a 30-fold increase above Input, followed by MVA-Vero with 5-fold increase above Input.

It is most interesting to compare the growth kinetics of the various viruses in human cell lines. Regarding reproductive replication in 143B cells (human bone cancer cell line) it was demonstrated that MVA-Vero was the only strain to show amplification above Input (3-fold increase). All other viruses did not amplify above Input, however there was a big difference between the MVA-HLR and both MVA-BN and MVA-575. MVA-HLR was "borderline" (1-fold decrease below Input), whereas MVA-BN exhibited the greatest attenuation (300-fold decrease below Input), followed by MVA-575 (59-fold decrease below Input). To summarize, MVA-BN is superior with respect to attenuation in human 143B cells.

Furthermore, concerning replication in HeLa cells (human cervix cancer cells) it was demonstrated that MVA-HLR amplified well in this cell line, and even better than it did in the permissive BHK cells (HeLa=125-fold increase above Input; BHK=88-fold increase above Input). MVA-Vero also amplified in this cell line (27-fold increase above Input). However, MVA-BN, and also to a lesser extent MVA-575, were attenuated in these cell lines (MVA-BN=29-fold decrease below Input and MVA-575=6-fold decrease below Input).

Concerning the replication in HaCaT cells (human keratinocyte cell line), it was demonstrated that MVA-HLR amplified well in this cell line (55-fold increase above Input). Both MVA-Vero adapted and MVA-575 exhibited amplification in this cell line (1.2 and 1.1-fold increase above Input, respectively). However, MVA-BN was the only one to demonstrate attenuation (5-fold decrease below Input).

From this experimental analysis, we may conclude that MVA-BN is the most attenuated strain in this group of viruses. MVA-BN demonstrates extreme attenuation in human cell lines by exhibiting an amplification ratio of 0.05 to 0.2 in human embryo kidney cells (293: ECACC No. 85120602) (data not incorporated in Table 1). Furthermore, it exhibits an amplification ratio of about 0.0 in 143B cells; an amplification ratio of about 0.04 in HeLa cells; and an amplification ratio of about 0.22 in HaCaT cells. Additionally, MVA-BN exhibits an amplification ratio of about 0.0 in CV1 cells. Amplification in Vero cells can be observed (ratio of 2.33), however, not to the same extent as in permissive cell lines such as BHK and CEF (compare to Table 1). Thus, MVA-BN is the only MVA strain exhibiting an amplification ratio of less than 1 in each human cell line examined, i.e., 143B, Hela, HaCaT, and 293. MVA-575 exhibits a profile similar to that of MVA-BN, however it is not as attenuated as MVA-BN.

MVA-HLR amplified well in all (human or otherwise) cell lines tested, except for 143B cells. Thus, it can be regarded as replication competent in all cell lines tested, with the exception of 143B cells. In one case, it even amplified better in a human cell line (HeLa) than in a permissive cell line (BHK).

MVA-Vero does exhibit amplification in all cell lines, but to a lesser extent than demonstrated by MVA-HLR (ignoring the 143B result). Nevertheless, it cannot be considered as being in the same "class" with regards to attenuation, as MVA-BN or MVA-575.

1.2 Replication In Vivo

Given that some MVA strains clearly replicate in vitro, different MVA strains were examined with regard to their ability to replicate in vivo using a transgenic mouse model AGR129. This mouse strain has targeted gene disruptions in the IFN receptor type I (IFN-α/β) and type II (IFN-γ) genes, and in RAG. Due to these disruptions, the mice have no IFN system and are incapable of producing mature B and T cells and, as such, are severely immune-compromised and highly susceptible to a replicating virus. Groups of six mice were immunized (i.p) with $10^7$ pfu of either MVA-BN, MVA-HLR or MVA-572 (used in 120,000 people in Germany) and monitored daily for clinical signs. All mice vaccinated with MVA-HLR or MVA-572 died within 28 and 60 days, respectively. At necropsy, there were general signs of severe viral infection in the majority of organs. A standard plaque assay measured the recovery of MVA ($10^8$ pfu) from the ovaries. In contrast, mice vaccinated with the same dose of MVA-BN (corresponding to the deposited strain ECACC V00083008) survived for more than 90 days and no MVA could be recovered from organs or tissues.

When taken together, data from the in vitro and in vivo studies clearly demonstrate that MVA-BN is more highly attenuated than the parental and commercial MVA-HLR strain, and may be safe for administration to immune-compromised subjects.

Example 2

Immunological and In Vivo Data in Animal Model Systems

These experiments were designed to compare different dose and vaccination regimens of MVA-BN compared to other MVAs in animal model systems.

2.1. Different Strains of MVA Differ in their Ability to Stimulate the Immune Response.

Replication competent strains of vaccinia induce potent immune responses in mice and at high doses are lethal. Although MVA are highly attenuated and have a reduced ability to replicate on mammalian cells, there are differences in the attenuation between different strains of MVA. Indeed, MVA-BN appears to be more attenuated than other MVA strains, even the parental strain MVA-575. To determine whether this difference in attenuation affects the efficacy of MVA to induce protective immune responses, different doses of MVA-BN and MVA-575 were compared in a lethal vaccinia challenge model. The levels of protection were measured by a reduction in ovarian vaccinia titres determined 4 days post challenge, as this allowed a quantitative assessment of different doses and strains of MVA.

Lethal Challenge Model

Specific pathogen-free 6-8-week-old female BALB/c (H-2d mice (n=5) were immunized (i.p.) with different doses ($10^2$, $10^4$ or $10^6$ TCID$_{50}$/ml) of either MVA-BN or MVA-575. MVA-BN and MVA-575 had been propagated on CEF cells, and had been sucrose purified and formulated in Tris pH 7.4. Three weeks later the mice received a boost of the same dose and strain of MVA, which was followed two weeks later by a lethal challenge (i.p.) with a replication competent strain of vaccinia. As replication competent vaccinia virus (abbreviated as "rVV") either the strain WR-L929 TK+ or the strain IHD-J were used. Control mice received a placebo vaccine. The protection was measured by the reduction in ovarian titres determined 4 days post challenge by standard plaque assay. For this, the mice were sacrificed on day 4 post the challenge and the ovaries were removed, homogenized in PBS (1 ml) and viral titres determined by standard plaque assay using VERO cells (Thomson, et al., 1998, J. Immunol. 160: 1717).

Figure 2:
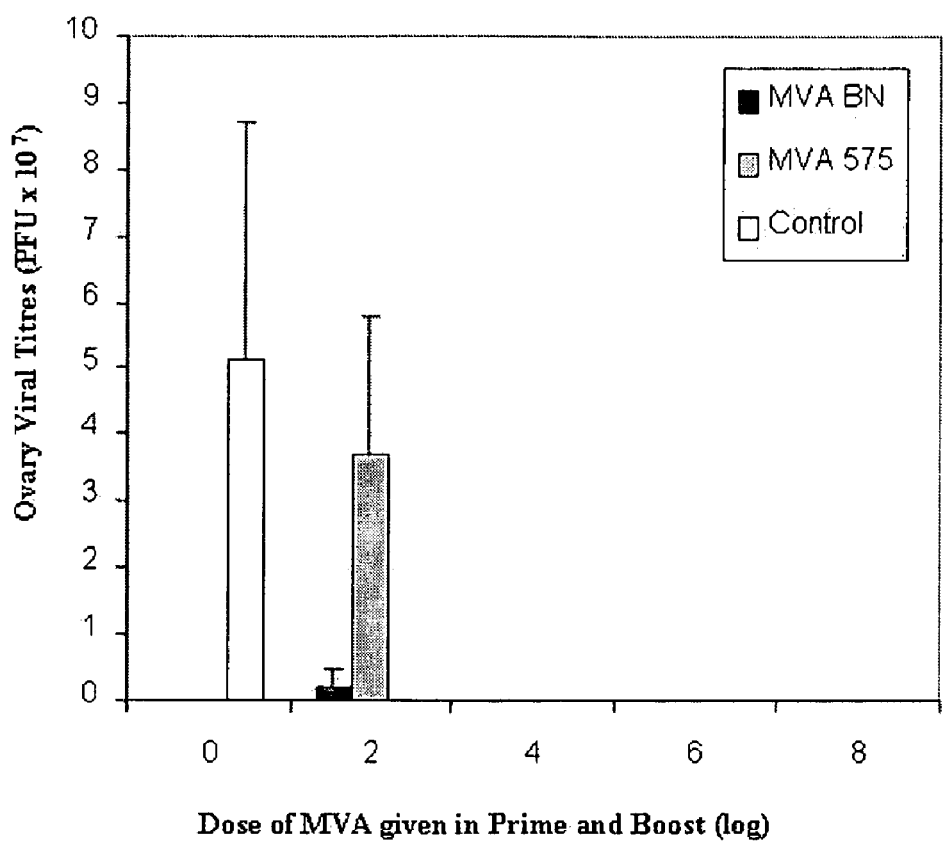

Mice vaccinated with two immunizations of either $10^4$ or $10^6$ TCID$_{50}$/ml of MVA-BN or MVA-575 were completely protected as judged by a 100% reduction in ovarian rVV titres 4 days post challenge (FIG. 2). The challenge virus was cleared. However, differences in the levels of protection afforded by MVA-BN or MVA-575 were observed at lower doses. Mice that received two immunizations of $10^2$ TCID$_{50}$/ml of MVA-575 failed to be protected, as judged by high ovarian rVV titres (mean $3.7 \times 10^7$ pfu+/−$2.11 \times 10^7$). In contrast, mice vaccinated with the same dose of MVA-BN exhibited a significant reduction (96%) in ovarian rVV titres (mean $0.21 \times 10^7$ pfu+/−$0.287 \times 07$). The control mice that received a placebo vaccine had a mean viral titre of $5.11 \times 10^7$ pfu (+/−$3.59 \times 10^7$) (FIG. 2).

Both strains of MVA induce protective immune responses in mice against a lethal rVV challenge. Although both strains of MVA are equally efficient at higher doses, differences in their efficacy are clearly evident at sub-optimal doses. MVA-BN is more potent than its parent strain MVA-575 at inducing a protective immune response against a lethal rVV challenge, which may be related to the increased attenuation of MVA-BN compared to MVA-575.

2.2. MVA-BN in Prime/Boost Vaccination Regimes
2.2.1.: Induction of Antibodies to MVA Following Vaccination of Mice with Different Smallpox Vaccines The efficacy of MVA-BN was compared to other MVA and vaccinia strains previously used in the eradication of smallpox. These included single immunizations using the Elstree and Wyeth vaccinia strains produced in CEF cells and given via tail scarification, and immunizations using MVA-572 that was previously used in the smallpox eradication program in Germany. In addition, both MVA-BN and MVA-572 were compared as a pre-vaccine followed by Elstree via scarification. For each group eight BALB/c mice were used and all MVA vaccinations ($1 \times 10^7$ TCID$_{50}$) were given subcutaneous at week 0 and week 3. Two weeks following the boost immunization the mice were challenged with vaccinia (IHD-J) and the titres in the ovaries were determined 4 days post challenge. All vaccines and regimes induced 100% protection.

The immune responses induced using these different vaccines or regimes were measured in animals prior to challenge. Assays to measure levels of neutralizing antibodies, T cell proliferation, cytokine production (IFN-γ vs IL-4) and IFN-γ production by T cells were used. The level of the T cell responses induced by MVA-BN, as measured by ELISPOT, was generally equivalent to other MVA and vaccinia viruses demonstrating bio-equivalence. A weekly analysis of the antibody titres to MVA following the different vaccination regimes revealed that vaccinations with MVA-BN significantly enhanced the speed and magnitude of the antibody response compared to the other vaccination regimes (FIG. 4). Indeed, the antibody titres to MVA were significantly higher (p>0.05) at weeks 2, 4 and 5 (1 week post boost at week 4) when vaccinated with MVA-BN compared to mice vaccinated with MVA-572. Following the boost vaccination at week 4, the antibody titres were also significantly higher in the MVA-BN group compared to the mice receiving a single vaccination of either the vaccinia strains Elstree or Wyeth. These results clearly demonstrate that 2 vaccinations with MVA-BN induced a superior antibody response compared to the classical single vaccination with traditional vaccinia strains (Elstree and Wyeth) and confirm the findings from section 1.5 that MVA-BN induces a higher specific immunity than other MVA strains.

2.2.2.: MVA-Prime and Boost Regimes Generate the Same Level of Protection as DNA-Prime/MVA-Boost Regimes in an Influenza Challenge Model.

The efficacy of MVA prime/boost regimes to generate high avidity CTL responses was assessed and compared to DNA prime/MVA boost regimes that have been reported to be superior. The different regimes were assessed using a murine polytope construct encoded by either a DNA vector or MVA-BN and the levels of CTL induction were compared by ELISPOT; whereas the avidity of the response was measured as the degree of protection afforded following a challenge with influenza.

Constructs

The DNA plasmid encoding the murine polytope (10 CTL epitopes including influenza, ovalbumin) was described previously (Thomson, et al., 1998, J. Immunol. 160: 1717). This murine polytope was inserted into deletion site 11 of MVA-BN, propagated on CEF cells, sucrose purified and formulated in Tris pH 7.4.

Vaccination Protocols

In the current study, specific pathogen free 6-8 week old female BALB/c (H-2d) mice were used. Groups of 5 mice were used for ELISPOT analysis, whereas 6 mice per group were used for the influenza challenge experiments. Mice were vaccinated with different prime/boost regimes using MVA or DNA encoding the murine polytope, as detailed in the results. For immunizations with DNA, mice were given a single injection of 50 μg of endotoxin-free plasmid DNA (in 50 μl of PBS) in the quadricep muscle. Primary immunizations using MVA were done either by intravenous administration of $10^7$ pfu MVA-BN per mouse, or by subcutaneous administration of $10^7$ pfu or $10^8$ pfu MVA-BN per mouse. Boost immunizations were given three weeks post primary immunization. Boosting with plasmid DNA was done in the same way as the primary immunization with DNA (see above). In order to establish CTL responses, standard ELISPOT assays (Schneider et al., 1998, Nat. Med. 4; 397-402) were performed on splenocytes 2 weeks after the last booster immunization using the influenza CTL epitope peptide (TYQ), the P. berghei epitope peptide (SYI), the Cytomegalovirus peptide epitope (YPH) and/or the LCV peptide epitope (RPQ).

For the challenge experiments, mice were infected i.n. with a sub-lethal dose of influenza virus, Mem71 ($4.5 \times 10^5$ pfu in 50 ml PBS). At day 5 post-infection, the lungs were removed and viral titres were determined in duplicate on Madin-Darby canine kidney cell line using a standard influenza plaque assay.

Figure 3:
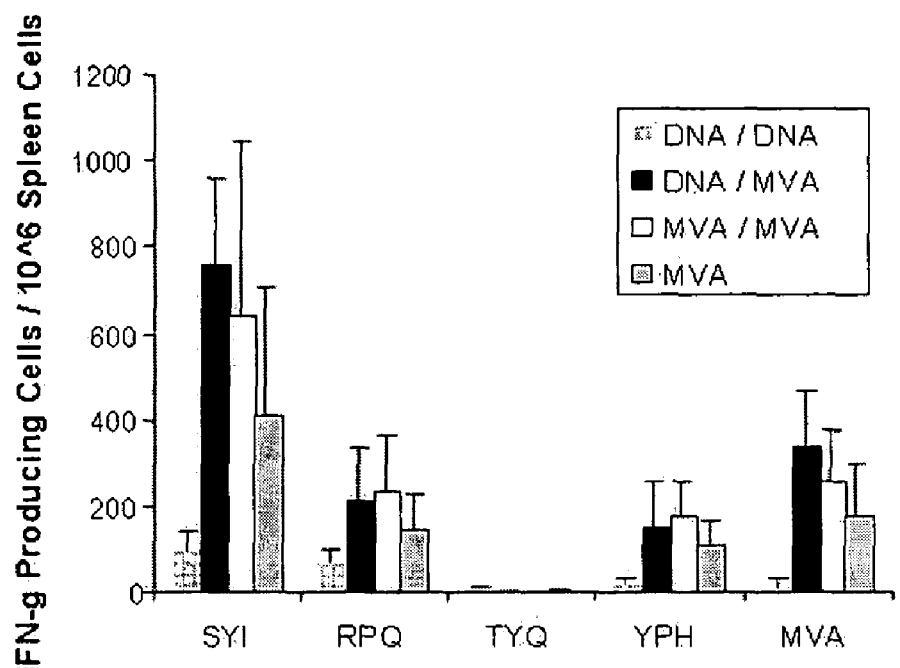
Figure 3:
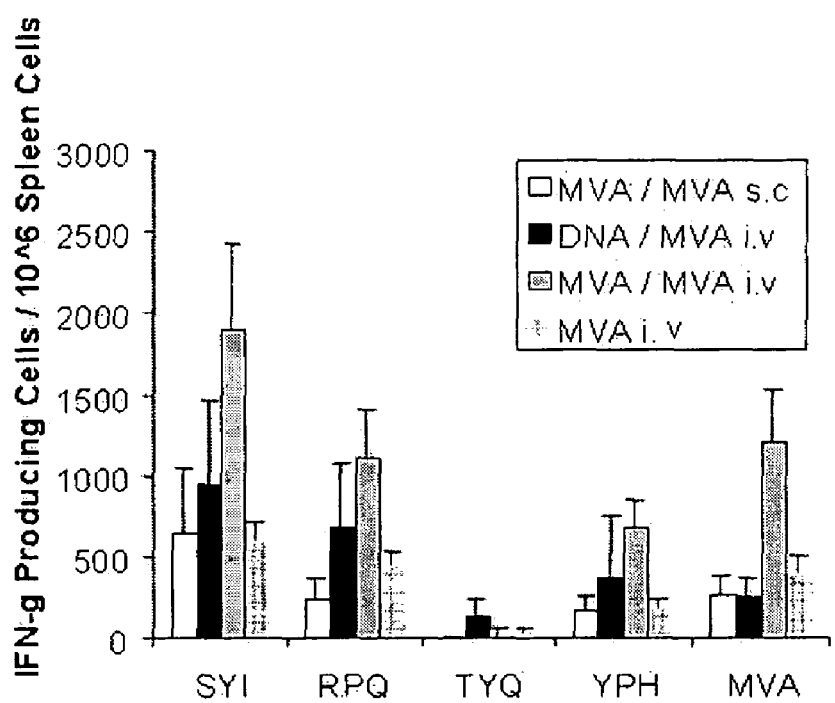

Results:

Using the DNA vaccine alone, the induction of CTL to the 4H-2d epitopes encoded by the murine polytope was poor and only weak responses could be detected to two of the epitopes for P. Berghei (SYI) and lymphocytic choriomeningitis virus (RPQ). In contrast, using a DNA prime/MVA boost regime ($10^7$ pfu MVA-BN given subcutaneous) there were significantly more CTL induced to SLY (8-fold increase) and RPQ (3-fold increase) and responses were also observed to a third epitope for murine cytomegalovirus (YPH) (FIG. 3A). However, $10^7$ pfu MVA-BN given subcutaneous in a homologous prime/boost regime induced the same level of response as DNA followed by MVA-BN (FIG. 3A). Surprisingly, there was no significant difference in the numbers of CTLs induced to the three epitopes when one immunization of MVA-BN ($10^7$ TCID$_{50}$) was used, indicating that a secondary immunization with MVA-BN did not significantly boost CTL responses.

Figure 3C:
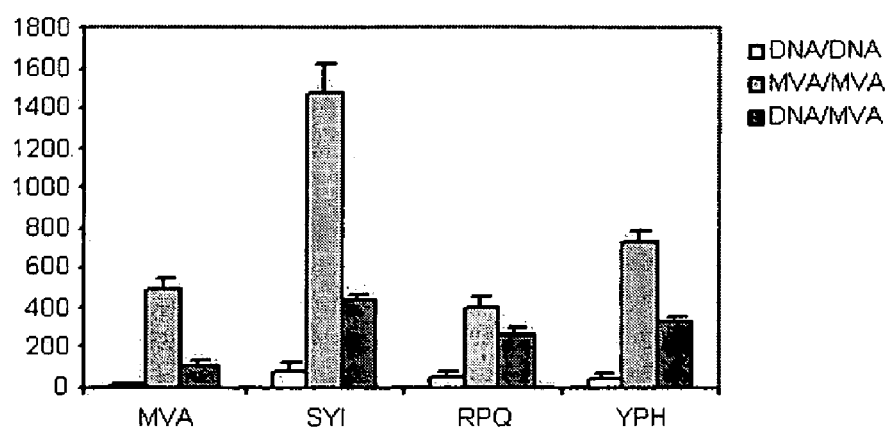

The subcutaneous administration of $10^7$ pfu MVA has previously been shown to be the most inefficient route and virus concentration for vaccination using other strains of MVA; particularly when compared to intravenous immunizations (Schneider, et al. 1998). In order to define optimal immunization regimes, the above protocol was repeated using various amounts of virus and modes of administration. In one experiment, $10^7$ pfu MVA-BN was given intravenously (FIG. 3B). In another experiment, $10^8$ pfu MVA-BN was administered subcutaneous (FIG. 3C). In both of these experiments, MVA-BN prime/boost immunizations induced higher mean CTL numbers to all three CTL epitopes when compared to DNA prime/MVA boost regimes. Also unlike $10^7$ pfu MVA-BN administered subcutaneous, immunization with $10^7$ pfu MVA-BN given intravenously and immunization with $10^8$ pfu given subcutaneous significantly boosted the CTL response. This clearly indicates that MVA-BN can be used to boost CTL responses in the presence of a pre-existing immunity to the vector.

TABLE 1

|  | CEF | HeLa | HaCaT | 143B | BHK | Vero | CV-1 |
|---|---|---|---|---|---|---|---|
| MVA-BN | 579.73 | 0.04 | 0.22 | 0.00 | 65.88 | 2.33 | 0.00 |
| MVA-575 | 796.53 | 0.15 | 1.17 | 0.02 | 131.22 | 10.66 | 0.06 |
| MVA-HLR | 86.68 | 124.97 | 59.09 | 0.83 | 87.86 | 34.97 | 29.70 |
| MVA-Vero | 251.89 | 27.41 | 1.28 | 2.91 | 702.77 | 1416.46 | 4.48 |

Virus amplification above the input level after 4 days infection
Amplification ratio = output TCID$_{50}$ − input TCID$_{50}$.
Values are in TCID$_{50}$.

The invention claimed is:

1. A method for inducing an immune response in a human patient comprising:
   (a) administering to the patient a priming inoculation of an effective amount of MVA-BN virus or derivative thereof, wherein the MVA-BN virus or derivative thereof is characterized by reproductive replication in vitro in chicken embryo fibroblasts and by being non-replicative in vitro in human cell lines selected from the human keratinocyte cell line HaCaT, the human embryo kidney cell line 293, the human bone osteosarcoma cell line 143B, and the human cervix adenocarcinoma cell line HeLa; and
   (b) administering to the patient a boosting inoculation of an effective amount of the MVA-BN virus or derivative thereof.

2. The method of claim 1, wherein the MVA-BN is as deposited at the European Collection of Cell Cultures (ECACC), Salisbury (UK) under number V00083008.

3. The method of claim 1, wherein the MVA-BN virus or derivative thereof comprises a heterologous nucleic acid sequence.

4. The method of claim 3, wherein the heterologous nucleic acid sequence is selected from a sequence encoding at least one antigen, antigenic epitope, or a therapeutic compound.

5. The method of claim 4, wherein the antigen or antigenic epitope is derived from a virus selected from an Influenza virus, a Flavivirus, a Paramyxovirus, a Hepatitis virus, a Cytomegalovirus, a Human immunodeficiency virus (HIV) or a virus causing hemorrhagic fever.

6. The method of claim 5, wherein the antigen or antigenic epitope comprises nef.

7. The method of claim 5, wherein an immune response is directed against HIV.

8. The method of claim 1, wherein the MVA-BN virus or derivative thereof is administered as a vaccine.

9. The method of claim 1, wherein the immune response is cross-reactive with smallpox.

10. The method of claim 1, wherein the patient is immune compromised.

11. The method of claim 1, wherein the patient exhibits preexisting immunity to MVA.

12. The method of claim 1, wherein the MVA-BN virus or derivative thereof is administered by intravenous, intramuscular, or subcutaneous injection.

13. The method of claim 1, wherein the prime/boost inoculation regime induces at least the same level of immune response when compared to a DNA-prime/vaccinia virus boost inoculation regime.

14. The method of claim 1, wherein the MVA-BN virus or derivative thereof is administered at a dose of at least about $1 \times 10^8$ TCID$_{50}$.

15. The method of claim 1, wherein the priming inoculation is administered about 4 weeks prior to the boosting inoculation.

16. A method for inducing an immune response in a mammal comprising:
   (a) administering to the mammal a priming inoculation of an effective amount of MVA-BN virus or derivative thereof, wherein the MVA-BN virus or derivative thereof is characterized by reproductive replication in vitro in chicken embryo fibroblasts and by being non-replicative in vitro in human cell lines selected from the human keratinocyte cell line HaCaT, the human embryo kidney cell line 293, the human bone osteosarcoma cell line 143B, and the human cervix adenocarcinoma cell line HeLa; and
   (b) administering to the mammal a boosting inoculation of an effective amount of the MVA-BN virus or derivative thereof.

* * * * *

UNITED STATES PATENT AND TRADEMARK OFFICE
CERTIFICATE OF CORRECTION

PATENT NO.       : 7,923,017 B2
APPLICATION NO.  : 11/977808
DATED            : April 12, 2011
INVENTOR(S)      : Chaplin et al.

It is certified that error appears in the above-identified patent and that said Letters Patent is hereby corrected as shown below:

Col. 19:

Line 50, Claim 1, replace "of MVA-BN virus" with -- of a MVA-BN virus --.

Signed and Sealed this
Thirty-first Day of May, 2011

David J. Kappos
*Director of the United States Patent and Trademark Office*